US011471087B2

(12) United States Patent
Rhodes et al.

(10) Patent No.: US 11,471,087 B2
(45) Date of Patent: Oct. 18, 2022

(54) INTEGRITY VERIFICATION SYSTEM FOR TESTING HIGH CHANNEL COUNT NEUROMONITORING RECORDING EQUIPMENT

(71) Applicant: Cadwell Laboratories, Inc., Kennewick, WA (US)

(72) Inventors: Ethan Rhodes, Benton City, WA (US); Richard A. Villarreal, West Richland, WA (US); John A. Cadwell, Richland, WA (US); Rose Rehfeldt, Kennewick, WA (US)

(*) Notice: Subject to any disclaimer, the term of this patent is extended or adjusted under 35 U.S.C. 154(b) by 306 days.

(21) Appl. No.: 16/678,482

(22) Filed: Nov. 8, 2019

(65) Prior Publication Data

US 2020/0146581 A1 May 14, 2020

Related U.S. Application Data

(60) Provisional application No. 62/758,320, filed on Nov. 9, 2018.

(51) Int. Cl.
*A61N 1/08* (2006.01)
*A61B 5/291* (2021.01)
(Continued)

(52) U.S. Cl.
CPC ............ *A61B 5/291* (2021.01); *A61B 5/7221* (2013.01); *A61N 1/08* (2013.01); *G01R 31/2812* (2013.01);
(Continued)

(58) Field of Classification Search
CPC ....... A61B 5/291; A61B 5/293; A61B 5/7221; A61B 5/7207; A61B 5/7217; A61N 1/08;
(Continued)

(56) References Cited

U.S. PATENT DOCUMENTS 751,475 A 2/1904 Vilbiss
2,320,709 A 6/1943 Arnesen
(Continued)

FOREIGN PATENT DOCUMENTS

CN 104766176 A 7/2015
DE 102014008684 A1 1/2016
(Continued)

OTHER PUBLICATIONS

Aage R. Møller, "Intraoperative Neurophysiologic Monitoring", University of Pittsburgh, School of Medicine Pennsylvania, © 1995 by Harwood Academic Publishers GmbH.
(Continued)

*Primary Examiner* — Tarun Sinha
*Assistant Examiner* — James I Burris
(74) *Attorney, Agent, or Firm* — Novel IP

(57) ABSTRACT

Methods of performing diagnostic tests on electroencephalography (EEG) recording devices comprising at least one stimulator coupled with a plurality of EEG electrode recording channels and corresponding recording channel connectors are performed by a test fixture comprising a plurality of resistors coupled with one or more of the EEG electrode recording channels and corresponding recording channel connectors. The methods include performing an impedance test for determining if each EEG recording channel of the EEG recording device has a predefined impedance, performing a channel uniqueness test for each EEG recording channel, performing a test for verifying the state of a switch of the stimulator of the EEG recording device, and performing a test for verifying connector IDs of the recording channel connectors connecting the EEG electrodes to respective EEG recording channels.

23 Claims, 13 Drawing Sheets

(51) Int. Cl.
*G01R 31/28* (2006.01)
*A61B 5/00* (2006.01)

(52) U.S. Cl.
CPC .... *G01R 31/2829* (2013.01); *A61N 2001/083* (2013.01)

(58) Field of Classification Search
CPC .............. A61N 1/3603; A61N 1/36128; A61N 2001/083; A61N 1/04; A61N 1/05; G01R 31/28; G01R 31/2812; G01R 31/2829
See application file for complete search history.

(56) References Cited

U.S. PATENT DOCUMENTS

| | | |
|---|---|---|
| 2,807,259 A | 9/1957 | Guerriero |
| 2,950,437 A * | 8/1960 | Stahl ................. G01R 31/2834 324/73.1 |
| 3,165,340 A | 1/1965 | Kuehl |
| 3,659,250 A | 4/1972 | Horton |
| 3,682,162 A | 8/1972 | Colyer |
| 3,985,125 A | 10/1976 | Rose |
| 3,993,859 A | 11/1976 | McNeel |
| 4,155,353 A | 5/1979 | Rea |
| 4,262,306 A | 4/1981 | Renner |
| 4,263,899 A | 4/1981 | Burgin |
| 4,545,374 A | 10/1985 | Jacobson |
| 4,562,832 A | 1/1986 | Wilder |
| 4,616,635 A | 10/1986 | Caspar |
| 4,705,049 A | 11/1987 | John |
| 4,716,901 A | 1/1988 | Jackson |
| 4,743,959 A | 5/1988 | Frederiksen |
| 4,765,311 A | 8/1988 | Kulik |
| 4,817,587 A | 4/1989 | Janese |
| 4,862,891 A | 9/1989 | Smith |
| 4,889,502 A | 12/1989 | Althouse |
| 4,914,508 A | 4/1990 | Music |
| 5,107,845 A | 4/1992 | Guern |
| 5,171,279 A | 12/1992 | Mathews |
| 5,196,015 A | 3/1993 | Neubardt |
| 5,284,153 A | 2/1994 | Raymond |
| 5,284,154 A | 2/1994 | Raymond |
| 5,299,563 A | 4/1994 | Seton |
| 5,377,667 A | 1/1995 | Patton |
| 5,438,989 A | 8/1995 | Hochman |
| 5,462,448 A | 10/1995 | Kida |
| 5,472,426 A | 12/1995 | Bonati |
| 5,474,558 A | 12/1995 | Neubardt |
| 5,540,235 A | 7/1996 | Wilson |
| 5,544,286 A | 8/1996 | Laney |
| 5,560,372 A | 10/1996 | Cory |
| 5,565,779 A | 10/1996 | Arakawa |
| 5,578,060 A | 11/1996 | Pohl |
| 5,601,608 A | 2/1997 | Mouchawar |
| 5,602,585 A | 2/1997 | Dickinson |
| 5,625,759 A | 4/1997 | Freeman |
| 5,648,815 A | 7/1997 | Toba |
| 5,664,029 A | 9/1997 | Callahan |
| 5,681,265 A | 10/1997 | Maeda |
| 5,684,887 A | 11/1997 | Lee |
| 5,728,046 A | 3/1998 | Mayer |
| 5,741,261 A | 4/1998 | Moskovitz |
| 5,766,133 A * | 6/1998 | Faisandier ............. A61B 5/276 600/509 |
| 5,772,661 A | 6/1998 | Michelson |
| 5,775,331 A | 7/1998 | Raymond |
| 5,775,931 A | 7/1998 | Jones |
| 5,785,648 A | 7/1998 | Min |
| 5,792,044 A | 8/1998 | Foley |
| 5,795,291 A | 8/1998 | Koros |
| 5,830,150 A | 11/1998 | Palmer |
| 5,847,755 A | 12/1998 | Wixson |
| 5,860,973 A | 1/1999 | Michelson |
| 5,868,668 A | 2/1999 | Weiss |
| 5,885,210 A | 3/1999 | Cox |
| 5,891,147 A | 4/1999 | Moskovitz |
| 5,928,139 A | 7/1999 | Koros |
| 5,928,158 A | 7/1999 | Aristides |
| 5,930,379 A | 7/1999 | Rehg |
| 5,931,777 A | 8/1999 | Sava |
| 5,933,929 A | 8/1999 | Kawakami |
| 5,944,658 A | 8/1999 | Koros |
| 5,954,635 A | 9/1999 | Foley |
| 5,993,385 A | 11/1999 | Johnston |
| 6,004,312 A | 12/1999 | Finneran |
| 6,004,341 A | 12/1999 | Zhu |
| 6,026,180 A | 2/2000 | Wittenstein |
| 6,042,540 A | 3/2000 | Johnston |
| 6,062,216 A | 5/2000 | Corn |
| 6,074,343 A | 6/2000 | Nathanson |
| 6,088,878 A | 7/2000 | Antonucci |
| 6,095,987 A | 8/2000 | Shmulewitz |
| 6,109,948 A | 8/2000 | Kuo |
| 6,116,941 A | 9/2000 | Kuo |
| 6,119,306 A | 9/2000 | Antonucci |
| 6,139,493 A | 10/2000 | Koros |
| 6,152,871 A | 11/2000 | Foley |
| 6,181,961 B1 | 1/2001 | Prass |
| 6,196,969 B1 | 3/2001 | Bester |
| 6,200,331 B1 * | 3/2001 | Swartz ................. A61N 1/3603 607/1 |
| 6,206,826 B1 | 3/2001 | Mathews |
| 6,210,202 B1 | 4/2001 | Kuo |
| 6,224,545 B1 | 5/2001 | Cocchia |
| 6,236,874 B1 | 5/2001 | Devlin |
| 6,241,548 B1 | 6/2001 | Kuo |
| 6,259,945 B1 | 7/2001 | Epstein |
| 6,264,491 B1 | 7/2001 | Lord |
| 6,266,558 B1 | 7/2001 | Gozani |
| 6,273,740 B1 | 8/2001 | Lord |
| 6,287,322 B1 | 9/2001 | Zhu |
| 6,302,842 B1 | 10/2001 | Auerbach |
| 6,306,100 B1 | 10/2001 | Prass |
| 6,309,349 B1 | 10/2001 | Bertolero |
| 6,325,764 B1 | 12/2001 | Griffith |
| 6,334,068 B1 | 12/2001 | Hacker |
| 6,373,890 B1 | 4/2002 | Freeman |
| 6,425,859 B1 | 7/2002 | Foley |
| 6,450,952 B1 | 9/2002 | Rioux |
| 6,466,817 B1 | 10/2002 | Kaula |
| 6,473,639 B1 | 10/2002 | Fischell |
| 6,500,128 B2 | 12/2002 | Marino |
| 6,535,759 B1 | 3/2003 | Epstein |
| 6,579,114 B2 | 6/2003 | Lord |
| 6,609,018 B2 | 8/2003 | Cory |
| 6,712,795 B1 | 3/2004 | Cohen |
| 6,799,931 B2 | 10/2004 | Kwilosz |
| 6,805,668 B1 | 10/2004 | Cadwell |
| 6,837,716 B1 | 1/2005 | Brazas |
| 6,847,849 B2 | 1/2005 | Mamo |
| 6,851,430 B2 | 2/2005 | Tsou |
| 6,869,301 B2 | 3/2005 | Shimizu |
| 6,870,109 B1 | 3/2005 | Villarreal |
| 6,926,728 B2 | 8/2005 | Zucherman |
| 6,945,933 B2 | 9/2005 | Branch |
| 7,072,521 B1 | 7/2006 | Cadwell |
| 7,089,059 B1 | 8/2006 | Pless |
| 7,104,965 B1 | 9/2006 | Jiang |
| 7,177,677 B2 | 2/2007 | Kaula |
| 7,214,197 B2 | 5/2007 | Prass |
| 7,230,688 B1 | 6/2007 | Villarreal |
| 7,261,688 B2 | 8/2007 | Smith |
| 7,374,448 B1 | 5/2008 | Jepsen |
| 7,470,236 B1 | 12/2008 | Kelleher |
| 7,522,953 B2 | 4/2009 | Kaula |
| 7,713,210 B2 | 5/2010 | Byrd |
| 7,801,601 B2 | 9/2010 | Maschino |
| 7,914,350 B1 | 3/2011 | Bozich |
| 7,963,927 B2 | 6/2011 | Kelleher |
| 7,983,761 B2 | 7/2011 | Giuntoli |
| 8,147,421 B2 | 4/2012 | Farquhar |
| 8,160,694 B2 | 4/2012 | Salmon |
| 8,192,437 B2 | 6/2012 | Simonson |
| D670,656 S | 11/2012 | Jepsen |

(56) References Cited

U.S. PATENT DOCUMENTS

| | | | |
|---|---|---|---|
| 8,323,208 B2 | 12/2012 | Davis | |
| 8,439,703 B2 | 5/2013 | Natoli | |
| 8,876,813 B2 | 11/2014 | Min | |
| 8,942,797 B2 | 1/2015 | Bartol | |
| 8,958,869 B2 | 2/2015 | Kelleher | |
| 9,084,551 B2 | 7/2015 | Brunnett | |
| 9,138,586 B2 | 9/2015 | Eiger | |
| 9,155,503 B2 | 10/2015 | Cadwell | |
| 9,295,401 B2 | 3/2016 | Cadwell | |
| 9,352,153 B2 | 5/2016 | Van Dijk | |
| 9,730,634 B2 | 8/2017 | Cadwell | |
| 10,238,467 B2 | 3/2019 | Cadwell | |
| 2001/0049510 A1 | 12/2001 | Burr | |
| 2002/0007188 A1 | 1/2002 | Arambula | |
| 2002/0009916 A1 | 1/2002 | Lord | |
| 2002/0088098 A1 | 7/2002 | Bouley | |
| 2002/0095080 A1 | 7/2002 | Cory | |
| 2003/0045808 A1 | 3/2003 | Kaula | |
| 2003/0074033 A1 | 4/2003 | Pless | |
| 2004/0030258 A1 | 2/2004 | Williams | |
| 2004/0127810 A1 | 7/2004 | Sackellares | |
| 2004/0192100 A1 | 9/2004 | Shimizu | |
| 2005/0003682 A1 | 1/2005 | Brazas | |
| 2005/0075578 A1 | 4/2005 | Gharib | |
| 2005/0085743 A1 | 4/2005 | Hacker | |
| 2005/0148927 A1 | 7/2005 | Ludin | |
| 2005/0182454 A1 | 8/2005 | Gharib | |
| 2005/0182456 A1 | 8/2005 | Ziobro | |
| 2005/0277844 A1 | 12/2005 | Strother | |
| 2006/0009754 A1 | 1/2006 | Boese | |
| 2006/0085048 A1 | 4/2006 | Cory | |
| 2006/0085049 A1 | 4/2006 | Cory | |
| 2006/0122514 A1 | 6/2006 | Byrd | |
| 2006/0135877 A1 | 6/2006 | Giftakis | |
| 2006/0258951 A1 | 11/2006 | Bleich | |
| 2006/0276720 A1 | 12/2006 | McGinnis | |
| 2007/0016097 A1 | 1/2007 | Farquhar | |
| 2007/0021682 A1 | 1/2007 | Gharib | |
| 2007/0032841 A1 | 2/2007 | Urmey | |
| 2007/0046471 A1 | 3/2007 | Nyalamadugu | |
| 2007/0049962 A1 | 3/2007 | Marino | |
| 2007/0184422 A1 | 8/2007 | Takahashi | |
| 2007/0202005 A1 | 8/2007 | Maschke | |
| 2008/0027507 A1 | 1/2008 | Bijelic | |
| 2008/0058606 A1 | 3/2008 | Miles | |
| 2008/0065144 A1 | 3/2008 | Marino | |
| 2008/0071191 A1 | 3/2008 | Kelleher | |
| 2008/0082136 A1 | 4/2008 | Gaudiani | |
| 2008/0097164 A1 | 4/2008 | Miles | |
| 2008/0108244 A1 | 5/2008 | Jepsen | |
| 2008/0167574 A1 | 7/2008 | Farquhar | |
| 2008/0183096 A1 | 7/2008 | Snyder | |
| 2008/0194970 A1 | 8/2008 | Steers | |
| 2008/0269777 A1 | 10/2008 | Appenrodt | |
| 2008/0281313 A1 | 11/2008 | Fagin | |
| 2008/0312520 A1 | 12/2008 | Rowlandson | |
| 2009/0018399 A1 | 1/2009 | Martinelli | |
| 2009/0088660 A1 | 4/2009 | McMorrow | |
| 2009/0105604 A1 | 4/2009 | Bertagnoli | |
| 2009/0177112 A1 | 7/2009 | Gharib | |
| 2009/0196471 A1 | 8/2009 | Goetz | |
| 2009/0204016 A1 | 8/2009 | Gharib | |
| 2009/0209879 A1 | 8/2009 | Kaula | |
| 2009/0259108 A1 | 10/2009 | Miles | |
| 2009/0279767 A1 | 11/2009 | Kukuk | |
| 2010/0036384 A1 | 2/2010 | Gorek | |
| 2010/0106011 A1 | 4/2010 | Byrd | |
| 2010/0113898 A1 | 5/2010 | Kim | |
| 2010/0152604 A1 | 6/2010 | Kaula | |
| 2010/0168603 A1 | 7/2010 | Himes | |
| 2010/0191305 A1 | 7/2010 | Imran | |
| 2010/0249638 A1 | 9/2010 | Liley | |
| 2010/0286554 A1 | 11/2010 | Davis | |
| 2010/0317931 A1 | 12/2010 | Sarkela | |
| 2010/0317989 A1 | 12/2010 | Gharib | |
| 2011/0082383 A1 | 4/2011 | Cory | |
| 2011/0184308 A1 | 7/2011 | Kaula | |
| 2011/0295579 A1 | 12/2011 | Tang | |
| 2011/0313530 A1 | 12/2011 | Gharib | |
| 2012/0003862 A1 | 1/2012 | Newman | |
| 2012/0071779 A1 | 3/2012 | Sarkela | |
| 2012/0109000 A1 | 5/2012 | Kaula | |
| 2012/0109004 A1 | 5/2012 | Cadwell | |
| 2012/0209082 A1 | 8/2012 | Al-Ali | |
| 2012/0209346 A1 | 8/2012 | Bikson | |
| 2012/0220891 A1 | 8/2012 | Kaula | |
| 2012/0238855 A1 | 9/2012 | Lanning | |
| 2012/0238893 A1 | 9/2012 | Farquhar | |
| 2012/0265040 A1 | 10/2012 | Ito | |
| 2012/0296230 A1 | 11/2012 | Davis | |
| 2013/0012880 A1 | 1/2013 | Blomquist | |
| 2013/0109996 A1 | 5/2013 | Turnbull | |
| 2013/0138010 A1 | 5/2013 | Nierenberg | |
| 2013/0152657 A1 | 6/2013 | Swinehart | |
| 2013/0204315 A1 | 8/2013 | Wongsarnpigoon | |
| 2013/0253447 A1 | 9/2013 | Ball | |
| 2013/0304407 A1 | 11/2013 | George | |
| 2014/0121555 A1 | 5/2014 | Scott | |
| 2014/0275926 A1 | 9/2014 | Scott | |
| 2014/0276181 A1 | 9/2014 | Sun | |
| 2015/0150512 A1 | 6/2015 | Warner | |
| 2015/0230749 A1 | 8/2015 | Gharib | |
| 2015/0351643 A1 | 12/2015 | Edwards | |
| 2015/0372433 A1 | 12/2015 | Lisogurski | |
| 2016/0000382 A1 | 1/2016 | Jain | |
| 2016/0174861 A1 | 6/2016 | Cadwell | |
| 2016/0270679 A1 | 9/2016 | Mahon | |
| 2016/0328991 A1 | 11/2016 | Simpson | |
| 2017/0100047 A1 | 4/2017 | Edwards | |
| 2018/0117309 A1 | 5/2018 | Rapoport | |
| 2018/0161123 A1 | 6/2018 | Cadwell | |
| 2018/0198218 A1 | 7/2018 | Regan | |
| 2018/0256097 A1 | 9/2018 | Bray | |
| 2018/0296277 A1 | 10/2018 | Schwartz | |
| 2019/0190187 A1 | 6/2019 | Fukazawa | |
| 2020/0022603 A1 | 1/2020 | Cardenas | |
| 2020/0108246 A1 | 4/2020 | Cadwell | |
| 2020/0297282 A1* | 9/2020 | Batzer | G01R 31/001 |
| 2020/0330772 A1 | 10/2020 | Hartmann-Bax | |

FOREIGN PATENT DOCUMENTS

| | | |
|---|---|---|
| EP | 298268 | 1/1989 |
| EP | 0863719 A1 | 9/1998 |
| EP | 890341 | 1/1999 |
| EP | 972538 | 1/2000 |
| EP | 1182965 B1 | 3/2002 |
| EP | 2173238 A2 | 4/2010 |
| JP | H11513592 A | 11/1999 |
| JP | 2008546509 A | 12/2008 |
| WO | 2000038574 A1 | 7/2000 |
| WO | 2000066217 A1 | 11/2000 |
| WO | 2001037728 A1 | 5/2001 |
| WO | 2003005887 A2 | 1/2003 |
| WO | 2005030318 A1 | 4/2005 |
| WO | 2006042241 A2 | 4/2006 |
| WO | 2016028822 A1 | 2/2016 |
| WO | 2016105571 A1 | 6/2016 |

OTHER PUBLICATIONS

Clements, et al., "Evoked and Spontaneous Electromyography to Evaluate Lumbosacral Pedicle Screw Placement", 21 (5):600-604 (1996).

Danesh-Clough, et al., "The Use of Evoked EMG in Detecting Misplaced Thoracolumbar Pedicle Screws", 26(12):1313-1316 (2001).

Dezawa et al., "Retroperitoneal Laparoscopic Lateral Approach to the Lumbar Spine: A New Approach, Technique, and Clinical Trial", Journal of Spinal Disorders 13(2):138-143 (2000).

Dickman, et al., "Techniques in Neurosurgery", National Library of Medicine, 3 (4) 301-307 (1997).

(56) References Cited

OTHER PUBLICATIONS

Epstein, et al., "Evaluation of Intraoperative Somatosensory-Evoked Potential Monitoring During 100 Cervical Operations", 18(6):737-747 (1993), J.B. Lippincott Company.
Glassman, et al., "A Prospective Analysis of Intraoperative Electromyographic Monitoring of Pedicle Screw Placement with Computed Tomographic Scan Confirmation", 20(12):1375-1379.
Goldstein, et al., "Minimally Invasive Endoscopic Surgery of the Lumbar Spine", Operative Techniques in Orthopaedics, 7 (1):27-35 (1997).
Greenblatt, et al., "Needle Nerve Stimulator-Locator", 41 (5):599-602 (1962).
H.M. Mayer, "Minimally Invasive Spine Surgery, A Surgical Manual", Chapter 12, pp. 117-131 (2000).
Hinrichs, et al., "A trend-detection algorithm for intraoperative EEG monitoring", Med. Eng. Phys. 18 (8):626-631 (1996).
Bergey et al., "Endoscopic Lateral Transpsoas Approach to the Lumbar Spine", SPINE 29 (15):1681-1688 (2004).
Holland, "Spine Update, Intraoperative Electromyography During Thoracolumbar Spinal Surgery", 23 (17):1915-1922 (1998).
Holland, et al., "Continuous Electromyographic Monitoring to Detect Nerve Root Injury During Thoracolumbar Scoliosis Surgery", 22 (21):2547-2550 (1997), Lippincott-Raven Publishers.
Hovey, A Guide to Motor Nerve Monitoring, pp. Mar. 1-31, 20, 1998, The Magstim Company Limited.
Kevin T. Foley, et al., "Microendoscipic Discectomy" Techniques in Neurosurgery, 3:(4):301-307, © 1997 Lippincott-Raven Publishers, Philadelphia.
Kossmann et al., "The use of a retractor system (SynFrame) for open, minimal invasive reconstruction of the anterior column of the thoracic and lumbar spine", 10:396-402 (2001).
Kossmann, et al., "Minimally Invasive Vertebral Replacement with Cages in Thoracic and Lumbar Spine", European Journal of Trauma, 2001, No. 6, pp. 292-300.
Lenke, et al., "Triggered Electromyographic Threshold for Accuracy of Pedicle Screw Placement, An Animal Model and Clinical Correlation", 20 (14):1585-1591 (1995).
Lomanto et al., "7th World Congress of Endoscopic Surgery" Singapore, Jun. 1-4, 2000 Monduzzi Editore S.p.A.; email: monduzzi@monduzzi.com, pp. 97-103 and 105-111.
Maguire, et al., "Evaluation of Intrapedicular Screw Position Using Intraoperative Evoked Electromyography", 20 (9):1068-1074 (1995).
Mathews et al., "Laparoscopic Discectomy With Anterior Lumbar Interbody Fusion, A Preliminary Review", 20 (16):1797-1802, (1995), Lippincott-Raven Publishers.
Bertagnoli, et al., "The AnteroLateral transPsoatic Approach (Alpa), A New Technique for Implanting Prosthetic Disc-Nucleus Devices", 16 (4):398-404 (2003).
Michael R. Isley, et al., "Recent Advances in Intraoperative Neuromonitoring of Spinal Cord Function: Pedicle Screw Stimulation Techniques", Am. J. End Technol. 37:93-126 (1997).
Minahan, et al., "The Effect of Neuromuscular Blockade on Pedicle Screw Stimulation Thresholds" 25(19):2526-2530 (2000).
Pimenta et al., "Implante de prótese de nucleo pulposo: analise inicial", J Bras Neurocirurg 12 (2):93-96, (2001).
Raymond J. Gardocki, MD, "Tubular diskectomy minimizes collateral damage", AAOS Now, Sep. 2009 Issue, http://www.aaos.org/news/aaosnow/sep09/clinical12.asp.
Raymond, et al., "The NerveSeeker: A System for Automated Nerve Localization", Regional Anesthesia 17:151-162 (1992).
Reidy, et al., "Evaluation of electromyographic monitoring during insertion of thoracic pedicle screws", British Editorial Society of Bone and Joint Surgery 83 (7):1009-1014, (2001).
Rose et al., "Persistently Electrified Pedicle Stimulation Instruments in Spinal Instrumentation: Technique and Protocol Development", Spine: 22(3): 334-343 (1997).
Teresa Riordan "Patents; A businessman invents a device to give laparoscopic surgeons a better view of their worK", New York Times www.nytimes.com/2004/29/business/patents-businessman-invents-device-give-la (Mar. 2004).
Toleikis, et al., "The usefulness of Electrical Stimulation for Assessing Pedicle Screw Placements", Journal of Spinal Disorders, 13 (4):283-289 (2000).
U.Schick, et al., "Microendoscopic lumbar discectomy versus open surgery: an intraoperative EMG study", pp. 20-26, Published online: Jul. 31, 2001 © Springer-Verlag 2001.
Bose, et al., "Neurophysiologic Monitoring of Spinal Nerve Root Function During Instrumented Posterior Lumbar Spine Surgery", 27 (13):1440-1450 (2002).
Vaccaro, et al., "Principles and Practice of Spine Surgery", Mosby, Inc. ©2003, Chapter 21, pp. 275-281.
Vincent C. Traynelis, "Spinal arthroplasty", Neurosurg Focus 13 (2):1-7. Article 10, (2002).
Welch, et al., "Evaluation with evoked and spontaneous electromyography during lumbar instrumentation: a prospective study", J Neurosurg 87:397-402, (1997).
Zouridakis, et al., "A Concise Guide to Intraoperative Monitoring", Library of Congress card No. 00-046750, Chapters, p. 21, chapter 4, p. 58 and chapter 7 pp. 119-120.
Medtronic, "Nerve Integrity Monitor, Intraoperative EMG Monitor, User's Guide", Medtronic Xomed U.K. Ltd., Unit 5, West Point Row, Great Park Road, Almondsbury, Bristol B5324QG, England, pp. 1-39.
Chapter 9, "Root Finding and Nonlinear Sets of Equations", Chapter 9:350-354, http://www.nr.com.
Digitimer Ltd., 37 Hydeway, Welwyn Garden City, Hertfordshire. AL7 3BE England, email:sales@digitimer.com, website: www.digitimer.com, "Constant Current High Voltage Stimulator, Model DS7A, For Percutaneous Stimulation of Nerve and Muscle Tissue".
Ford et al., Electrical characteristics of peripheral nerve stimulators, implications for nerve localization, Dept. of Anesthesia, University of Cincinnati College of Medicine, Cincinnati, OH 45267, pp. 73-77.
Deletis et al., "The role of intraoperative neurophysiology in the protection or documentation of surgically induced injury to the spinal cord", Correspondence Address: Hyman Newman Institute for Neurology & Neurosurgery, Beth Israel Medical Center, 170 East End Ave., Room 311, NY 10128.
Urmey "Using the nerve stimulator for peripheral or plexus nerve blocks" Minerva Anesthesiology 2006; 72:467-71.
Butterworth et al., "Effects of Halothane and Enflurane on Firing Threshold of Frog Myelinated Axon", Journal of Physiology 411:493-516, (1989) From the Anesthesia Research Labs, Brigham and Women's Hospital, Harvard Medical School, 75 Francis St., Boston, MA 02115, jp.physoc.org.
Calancie, et al., "Threshold-level multipulse transcranial electrical stimulation of motor cortex for intraoperative monitoring of spinal motor tracts: description of method and comparison to somatosensory evoked potential monitoring" J Neurosurg 88:457-470 (1998).
Calancie, et al., "Threshold-level repetitive transcranial electrical stimulation for intraoperative monitoring of central motor conduction", J. Neurosurg 95:161-168 (2001).
Calancie, et al., Stimulus-Evoked EMG Monitoring During Transpedicular Lumbosacral Spine Instrumentation, Initial Clinical Results, 19 (24):2780-2786 (1994).
Carl T. Brighton, "Clinical Orthopaedics and Related Research", Clinical Orthopaedics and related research No. 384, pp. 82-100 (2001).
International Search Report for PCT/US2019/063793, dated Feb. 19, 2020.
International Search Report for PCT/US2017/062559, dated Jan. 26, 2018.
Brainstorm Website, http://neuroimage.usc.edu/brainstorm/ accessed online Oct. 9, 2021, available online Apr. 11, 2018. (Year: 2018).
Compumedics Website, "Compumedics Profusion EEG 4" accessed online Oct. 9, 2021, available online Feb. 23, 2017 (ttps://www.compumedics.com.au/wp-content/uploads/2016/08/AD125-02-Profusion-EEG4-brochureLR.pdf (Year:2017).
Intelimed Website, "Compumedics Profusion EEG 5 Top Features" accessed online Oct. 9, 2021, available online Sep. 30, 2014 2014).
Deff Corporation, No. more confusion about which direction to plug in. A Usb cable that can be plugged in both ways is now available. A connector is equipped with an LED indicator to check a charging

(56) References Cited

OTHER PUBLICATIONS status of a smartphone. Nov. 6, 2015 (Dec. 28, 2021 Search) Internet URL:https://deff.co.jp/news/dca-mbled (Document showing known technology).

"Long, S; "Phase Locked Loop Circuits", Apr. 27, 2005". (Year: 2005).

Brainstorm website, https://web.archive.org/web/20180421074035/ https://neuroimage.usc.edu/brainstorm/Tutorials/MontageEditor, available online Apr. 21, 2018 (Year: 2018).

Brainstorm website, https://web.archive.org/web/20180330235454/ http://neuroimage.usc.edu/brainstorm/Tutorials/CreateProtocol,) available on Mar. 30, 2018 (Year: 2018).

Brainstorm website,https://web.archive.Org/web/20180416072211/ http://neuroimage.usc.edu/brainstorm/Screenshots .available on Apr. 16, 2018 (Year: 2018).

Brainstorm website,https://web.archive.org/web/20180411211909/ https://neuroimage.usc.edu/brainstorm/lntroduction,available on Apr. 11, 2018 (Year: 2018).

Brainstorm website,https://web.archive.Org/web/20180505021718/ https://neuroimage.usc.edu/brainstorm/Tutorials/Epileptogenicity, available on May 5, 2018 (Year: 2018).

\* cited by examiner

INTEGRITY VERIFICATION SYSTEM FOR TESTING HIGH CHANNEL COUNT NEUROMONITORING RECORDING EQUIPMENT

CROSS-REFERENCE

The present application relies on U.S. Patent Provisional Application No. 62/758,320, entitled "Integrity Verification System for Testing High Channel Count Neuromonitoring Recording Equipment" and filed on Nov. 9, 2018, for priority, which is herein incorporated by reference in its entirety.

FIELD

The present specification is related generally to the field of electroencephalography (EEG), particularly electrocorticography (ECoG) and stereoelectroencephalography (sEEG). More specifically, the present specification is related to an integrity verification system (IVS) for verifying operational integrity of an ECoG or sEEG recording device prior to starting a neuromonitoring recording procedure.

BACKGROUND

Neuromonitoring is the use of electrophysiological methods, such as electroencephalography (EEG), electromyography (EMG), and evoked potentials, to monitor the functional integrity of certain neural structures (e.g., nerves, spinal cord and parts of the brain) during surgery. The purpose of neuromonitoring is to reduce the risk to the patient of iatrogenic damage to the nervous system, and/or to provide functional guidance to the surgeon and anesthesiologist, for example, to map the brain of epileptic patients to determine candidates for surgical treatment. Generally, neuromonitoring procedures such as EEG involve a large number of electrodes coupled to the human body. In an EEG procedure, the electrodes are used to record and monitor the electrical activity corresponding to various parts of the brain for detection and treatment of various ailments such as epilepsy, sleep disorders and coma. EEG procedures are either non-invasive or invasive. In non-invasive EEG, a number of electrodes are deployed on the human scalp for recording electrical activity in portions of the underlying brain. In invasive EEG, through surgical intervention, the electrodes are placed directly over sections of the brain, in the form of a strip or grid, or are positioned in the deeper areas of the brain. Each of these electrodes is coupled to a wire lead which, in turn, is connected to a control unit adapted to receive and transmit electrical signals. The electrical activity pattern captured by various electrodes is analyzed using standard algorithms to localize or spot the portion of brain which is responsible for causing the specific ailment.

The number of electrodes in EEG systems typically varies between 21 and 256 and can be more than 500. Increasing the number of electrodes in EEG procedures helps decrease the localization error and thus more ably assist the physician to better plan for surgical procedures. Accordingly, advanced EEG systems involve a high density electrode configuration with more than 256 electrodes for separately mapping the electrical activity corresponding to every portion of the brain. However, the overall set up and verification process becomes more time consuming and error prone as the number of electrodes increases in the EEG procedures. An error in the EEG data presented to the physician could have severe adverse effects on the patient involved. Thus, as the number of channels increase it is vital that the methods to verify a required functionality of the EEG equipment also increasingly improve in efficiency and efficacy.

In neuromonitoring, as each electrode is positioned at a different location to capture the electrical activity in its vicinity, the input recorded from each electrode has to be processed independently. The system is required to maintain the identity of each electrode and accordingly process the input received from that electrode. Surgical applications in EEG also use grid electrodes which inherently combine multiple leads (up to 16) into a single connector, which is then attached to an adapter with 16 individual leads, and then to an amplifier that has inputs for each individual channel.

An intracranial EEG procedure requires accurate information such as but not limited to electrode impedance values, and electrode contact viability from the EEG recording device being used. If the EEG recording device includes an integrated switch matrix for an internal or external cortical stimulator, the respective ON/OFF states of the recording channel switches and stimulator switches must also be functional and correct to provide accurate information to a physician. It is also important that each channel input is acting uniquely (i.e. no shorts between channels) and that each channel is designated correctly from the patient to the software. If the patient connections to the recording device use programmed unique identifiers to be correctly designated in the software, this functionality is also vital for providing accurate information to the physician.

Electrocorticography (ECoG) and stereoelectroencephalography (sEEG) are methods of EEG monitoring and cortical mapping that require high channel count recording and stimulating devices. In ECoG, electrodes are placed on the cerebral cortex via a craniotomy. In sEEG, depth electrodes may be placed via small holes (burr holes) drilled in the patient's skull. ECoG and sEEG may be used when standard EEG monitoring results are inconclusive, particularly for epilepsy patients. Since ECoG and sEEG use strip or grid electrodes and depth electrodes on the surface of the brain and in the brain respectively, they provide a benefit of using electrodes that are closer to the area(s) producing seizures than electrodes placed on the scalp in standard EEG monitoring. In addition, placed directly on or in the brain have the advantage of recording signals without the interference of skin, fat tissue, muscle or bone. ECoG and sEEG may be used to monitor, assess and map the brains of epilepsy patients who have may benefit from surgery and have not responded to less invasive treatments including pharmaceuticals. Mapping will indicate to physicians' areas of an epileptic brain for resection and functional areas of the brain to be safeguarded during surgery. Functional mapping involves using a cortical stimulator to generate stimulus through the electrodes (grid or strip) to stimulate the brain and record signals to identify the underlying function of a brain region, such as language, sensation, or motor function, to precisely map an origin of seizures. When a discrete epileptogenic region of the brain is identified and can be removed without the introduction of unacceptable additional neurological deficits, respective surgery is performed. Prior to performing this EEG monitoring, multiple aspects of a recording device with integrated recording channel and stimulator switch matrix must be tested to ensure the equipment is working as intended. This testing can be burdensome with large channel count systems.

Prior art patent publications disclose a number of methods of impedance measurement in an EEG recording device. US Patent Publication No. 20060020218 discloses "[a] method comprising: sending a test signal to a sensor of physiological data, said sensor having an impedance; receiving a combined signal comprising a physiological signal component and a test signal component; filtering the combined signal to separate the physiological signal component from the test signal component; and detecting changes in the impedance of the sensor by a comparison of test signal components."

WIPO Publication No. WO2018102855A1 discloses "[a] biological amplifier for measuring an electrical activity of nerve cells of a physiological function in a subject, comprising: (a) a plurality of electrodes, at least one of which is a sensor electrode for measuring the electrical activity, the or each sensor electrode adapted to be placed on the skin of the subject above the nerve cells, and (b) means for measuring contact impedance between the skin of the subject and the or each sensor electrode due to a voltage applied between the plurality of electrodes, wherein the contact impedance measuring means operates continuously and concurrently with the measuring of the electrical activity of the nerve cells of the physiological function by the biological amplifier."

Some prior art publications also disclose methods for measuring electrode lead integrity in EEG recording devices. US Patent Publication No. 20090299201 discloses "[a] method comprising: obtaining impedance trend data for an electrical path, the electrical path comprising a plurality of electrodes; obtaining additional diagnostic data that is associated with the electrical path, the additional diagnostic data being distinct from the impedance trend data; and combining both the impedance trend data and the additional diagnostic data into a displayable report that indicates whether there is a possible condition with the electrical path."

US Patent Publication No. 20100023084 discloses "[a] method comprising: sensing a physiological signal of a patient via one or more electrodes on at least one implantable medical lead; detecting saturation of the signal; and triggering a lead integrity test of the implantable medical lead in response to the detection."

Switching a cortical stimulator between multiple recording channels is described in US Patent Publication No. 20100298907A1 which discloses "[a] cortical stimulator system, comprising: a stimulation device having a switch configured to selectively control various electrodes; and a user interface device operatively connected to the stimulation device for controlling the electronic switch and stimulation device, the cortical stimulator system configured to provide a report of provided stimulation."

However, none of the prior art mentioned above disclose a verification system or an integrity verification system (IVS) which incorporates a hardware test fixture, associated hardware test circuitry, and software diagnostics for testing multiple aspects of an EEG recording device and integrated switch matrix. Hence, there is need for an IVS that can verify the functionality of impedance measurement, electrode contact viability measurement, both recording channel and stimulator switch ON/OFF states, channel uniqueness, and correct identification (ID) of the unique identifiers of the patient connections prior to beginning a procedure.

SUMMARY

The following embodiments and aspects thereof are described and illustrated in conjunction with systems, tools and methods, which are meant to be exemplary and illustrative, and not limiting in scope. The present application discloses numerous embodiments.

The present specification discloses a method of performing a diagnostic test on an electroencephalography (EEG) recording device, wherein the EEG recording device comprises 1) at least one stimulator coupled with a plurality of EEG electrode recording channels and 2) recording channel connectors connecting one or more EEG electrodes to the plurality of EEG electrode recording channels and wherein the diagnostic test is performed by a hardware testing device comprising a plurality of resistors coupled with one or more of the plurality of EEG electrode recording channels and corresponding recording channel connectors, the method comprising: performing an impedance test for determining if each EEG recording channel of the plurality of EEG electrode recording channels has a predefined impedance; performing a channel uniqueness test for each EEG recording channel of the plurality of EEG electrode recording channels; performing a test for verifying a state of a switch of the at least one stimulator of the EEG recording device; and performing a test for verifying correct functionality of connector identification detection and communication for electrode connections.

Optionally, the at least one stimulator comprises hardware test circuitry comprising a constant voltage test stimulator. Optionally, the constant voltage test stimulator comprises a stimulator anode to connect to the stimulator high side switches, a stimulator cathode to connect to the stimulator low side switches, and a ground connect for the constant voltage test stimulator. Optionally, performing a test for verifying the state of a switch of the stimulator of the EEG recording device comprises performing a test for verifying a state of the high side stimulator switches. Optionally, performing a test for verifying the state of a switch of the stimulator of the EEG recording device comprises performing a test for verifying a state of the low side stimulator switches. Optionally, performing a test for verifying the state of the high side stimulator switches comprises: connecting one of the high side simulator switches with one of the plurality of resistors of the hardware testing device; connecting the plurality of EEG electrode recording channels with the plurality of resistors of the hardware testing device; injecting a stimulus into the one of the high side simulator switches, wherein the stimulus is defined by a voltage or current level; measuring a voltage on the plurality of EEG electrode recording channels; verifying that the one of the high-side stimulator switches is connected with at least one of the plurality of resistors if the measured voltage is equal to the expected stimulus level; and verifying that the one of the high-side stimulator switches is not connected with any of the plurality of resistors, if the measured voltage is equal to a predefined fraction of the stimulus voltage. Optionally, wherein injecting the stimulus comprises injecting a constant-voltage stimulus. Optionally, injecting a stimulus comprises injecting a constant-current stimulus.

Optionally, performing a test for verifying the state of the low side stimulator switches comprises: connecting one of the high-side stimulator switches to one of the plurality of resistors and one of the low-side stimulator switches to one of the plurality of resistors; connecting the plurality of EEG electrode recording channels with the plurality of resistors; injecting a stimulus into the one of the high-side stimulator switches; measuring a voltage on at least one of the plurality of EEG electrode recording channels; and verifying that the one of the low-side stimulator switches is working if the measured voltage is at a ground potential. Optionally, injecting the stimulus comprises injecting a constant-voltage stimulus. Optionally, injecting a stimulus comprises injecting a constant-current stimulus.

The at least one stimulator may comprise a stimulator external to the EEG recording device.

Optionally, performing the channel uniqueness test for each of the plurality of EEG electrode recording channels includes performing a lead-off functionality test.

Optionally, performing the channel uniqueness test comprises: connecting the hardware testing device to the EEG recording device; connecting the plurality of resistors of the hardware testing device to the plurality of EEG electrode recording channels; determining if an electrode connected status is reported for each of the plurality of EEG electrode recording channels; and determining one or more of: a recording channel uniqueness, a recording channel component, or an electrode contact viability as not working as intended if an electrode connected status is not reported for each of the plurality of EEG electrode recording channels. Optionally, performing the channel uniqueness test further comprises: disconnecting one of the plurality of EEG electrode recording channels from one or more of the plurality of resistors of the hardware testing device and determining if an electrode disconnected status is reported for the disconnected one of the plurality of EEG electrode recording channels. Optionally, performing the channel uniqueness test further comprises: verifying one or more of a recording channel uniqueness, a recording channel component, or an electrode contact viability as not working as intended if an electrode disconnected status is not reported for the disconnected one of the plurality of EEG electrode recording channels; and determining a working status of the one of the plurality of EEG electrode recording channels if an electrode disconnected status is reported for the disconnected one of the plurality of EEG electrode recording channels.

Optionally, the method further comprises cycling through the plurality of EEG electrode recording channels using a diagnostic software running on a computing device coupled with the hardware testing device and the EEG recording device to verify a required functionality.

Optionally, performing a test for verifying a state of a switch of the at least one stimulator comprises verifying a state of device switches and integrated stimulation switch matrix switches.

Optionally, performing the impedance test comprises: connecting the hardware testing device to the EEG recording device; activating a mode within the EEG recording device to measure an impedance for each of the plurality of EEG electrode recording channels; determining if measured impedance values match expected impedance values within a predetermined margin of error; determining that the one or more of the plurality of EEG electrode recording channels are not working as intended if the measured impedance values do not match the expected impedance values within the predetermined margin of error; and verifying that the one or more of the plurality of EEG electrode recording channels are working as intended if the measured impedance values match the expected impedance values within the predetermined margin of error. Optionally, the predetermined margin of error is +/−30% of the expected impedance value.

Optionally, performing the test for verifying correct functionality of connector identification detection and communication for electrode connections comprises: connecting the hardware testing device to the EEG recording device; detecting a presence or absence of a connector identification circuitry with respect to predefined groups of the plurality of EEG electrode recording channels; determining if the connector identification circuitry is detected on the groups of the plurality of EEG electrode recording channels, wherein the detected connector identification circuitry comprises sequential, incrementing serial numbers corresponding to sequential groups of recording channels; determining the connector identification circuitry as not working as intended if the connector identification circuitry is not detected on the plurality of EEG electrode recording channels and comprises sequential, incrementing serial numbers; and verifying the connector identification circuitry as working as intended if the connector identification circuitry is detected on the plurality of EEG electrode recording channels and comprises sequential, incrementing serial numbers. Optionally, at least one of the connector identification circuitries has a polarity that is a reverse of a polarity of the other connector identification circuitries. Optionally, the plurality of EEG electrode recording channels is grouped into predefined groups of inputs for each side of the EEG recording device, wherein each of the predefined groups comprises 4 recording channels.

The present specification also discloses a method of performing diagnostic tests on an EEG recording device comprising at least one stimulator coupled with a plurality of EEG electrode recording channels and corresponding recording channel connectors connecting one or more EEG electrodes to the recording channels. The diagnostic tests are performed by a test fixture comprising a plurality of resistors coupled with one or more of the EEG electrode recording channels and corresponding recording channel connectors, the method comprising: performing an impedance test for determining if each EEG recording channel of the EEG recording device has a predefined impedance; performing a channel uniqueness test for each EEG recording channel; performing a test for verifying the state of a switch of the stimulator of the EEG recording device; and performing a test for verifying connector IDs of the recording channel connectors connecting the one or more EEG electrodes to respective EEG recording channels.

Optionally, the at least one stimulator comprises hardware test circuitry comprising a constant voltage test stimulator. The constant voltage test stimulator may comprise a stimulator anode, a stimulator cathode, a plurality of stimulator high side switches, a plurality of stimulator low side switches, and a ground connect for the voltage test stimulator. Optionally, performing a test for verifying the state of a switch of the stimulator of the EEG recording device comprises performing a test for verifying the state of the high side stimulator switches of the EEG recording device.

Optionally, performing a test for verifying the state of a switch of the stimulator of the EEG recording device comprises performing a test for verifying the state of the low side stimulator switches of the EEG recording device.

Optionally, performing a test for verifying the state of the high side stimulator switches of the EEG recording device comprises: connecting one high-side switch at a time with a resistor of the test fixture; connecting all the EEG recording channels with the test fixture resistors; injecting a stimulus into the connected high-side switch; measuring the voltage on all the EEG recording channels; verifying that the high-side stimulator switch is working as intended (connected) if the voltage on the connected high-side stimulator switch channel is equal to the constant voltage stimulus; and verifying that the high-side stimulator switches are not connected with any of the fixture resistors, if voltage on all other EEG recording channels is equal to a predefined fraction of the constant voltage stimulus.

Optionally, injecting a stimulus into the connected high-side switch comprises injecting a constant-voltage stimulus. Optionally, injecting a stimulus into the connected high-side switch comprises injecting a constant-current stimulus.

Optionally, performing a test for verifying the state of the low side stimulator switches of the EEG recording device comprises: connecting one high-side stimulator switch and one low-side stimulator switch at a time with a resistor of the test fixture; connecting all the EEG recording channels with the test fixture resistors; injecting a constant-voltage stimulus into the connected high-side switch; measuring the voltage on all the EEG recording channels; and verifying that the low-side stimulator switch is working as intended (connected), if the voltage on the connected low-side stimulator channel is at a ground potential.

Optionally, the at least one stimulator comprises an external stimulator. Optionally, performing a channel uniqueness test for each EEG recording channel includes a "lead-off" functionality test.

Optionally, performing a channel uniqueness test for each EEG recording channel comprises: connecting the test fixture to the EEG recording device; connecting the plurality of resistors of the hardware testing device to the recording channels of the EEG recording device; determining if a status of "electrode connected" is reported for each recording channel; verifying one or more of: a recording channel uniqueness, a recording channel component, or an electrode contact viability as 'not working as intended', if a status of "electrode connected" is not reported for each recording channel; disconnecting one recording channel from the plurality of resistors of the hardware testing device, if a status of "electrode connected" is reported for each recording channel; determining if a status of "electrode disconnected" is reported for the disconnected channel; verifying one or more of: a recording channel uniqueness, a recording channel component, or an electrode contact viability as 'not working as intended', if a status of "electrode disconnected" is not reported for the disconnected channel; and verifying an 'as intended' working of the recording channels of the EEG recording device, if a status of "electrode disconnected" is reported for the disconnected channel.

Optionally, verifying that a recording channel component is 'not working as intended' comprises verifying that a switch of the recording channel is 'not working as intended'. Optionally, when performing a channel uniqueness test for each EEG recording channel, the method further comprises the step of cycling through all of the recording channels using a diagnostic software running on a computing device coupled with the test fixture and the EEG recording device to verify a required functionality.

Optionally, performing a test for verifying the state of a switch of the stimulator of the EEG recording device includes verifying the state of device switches and integrated stimulation switch matrix switches.

Optionally, performing an impedance test for determining if each EEG electrode recording channel of the EEG recording device has a predefined impedance comprises: connecting the test fixture to the EEG recording device; activating an internal hardware test circuit of the test fixture to measure impedance for each EEG electrode recording channel; determining if the measured impedance values match an expected impedance value allowing for a predetermined margin of error; verifying that the electrode recording channels are 'not working as intended', if the measured impedance values do not match the expected impedance value allowing for a predetermined margin of error; and verifying that the electrode recording channels are 'working as intended', if all impedance values match the expected impedance value allowing for a predetermined margin of error. In an embodiment, the predetermined margin of error is +/−30% of the expected impedance value.

Optionally, performing a test for verifying connector IDs of the recording channel connectors connecting the one or more EEG electrodes to respective EEG recording channels comprises: connecting the test fixture to the EEG recording device; detecting the presence or absence of a connector identification circuitry with respect to each of predefined groups of recording channels; determining if the connector identification circuitry is detected on all the groups of recording channels, wherein the detected identification circuitry comprises sequential, incrementing serial numbers corresponding to sequential groups of recording channels; verifying the connector identification circuitry as 'not working as intended', if the identification circuitry is not detected on all groups of recording channels, and comprises sequential, incrementing serial numbers; and verifying the connector identification circuitry as 'working as intended' if the identification circuitry is detected on all groups of recording channels, and comprises sequential, incrementing serial numbers.

Optionally, at least one identification circuitry has a polarity reverse of the polarity of the remaining identification circuitry. Optionally, the recording channels are grouped into 18 groups of inputs recording channels for each side of the recording device, wherein each group comprises 4 recording channels.

The aforementioned and other embodiments of the present shall be described in greater depth in the drawings and detailed description provided below.

BRIEF DESCRIPTION OF THE DRAWINGS

These and other features and advantages of the present specification will be further appreciated, as they become better understood by reference to the following detailed description when considered in connection with the accompanying drawings.

DETAILED DESCRIPTION

Figure 1:
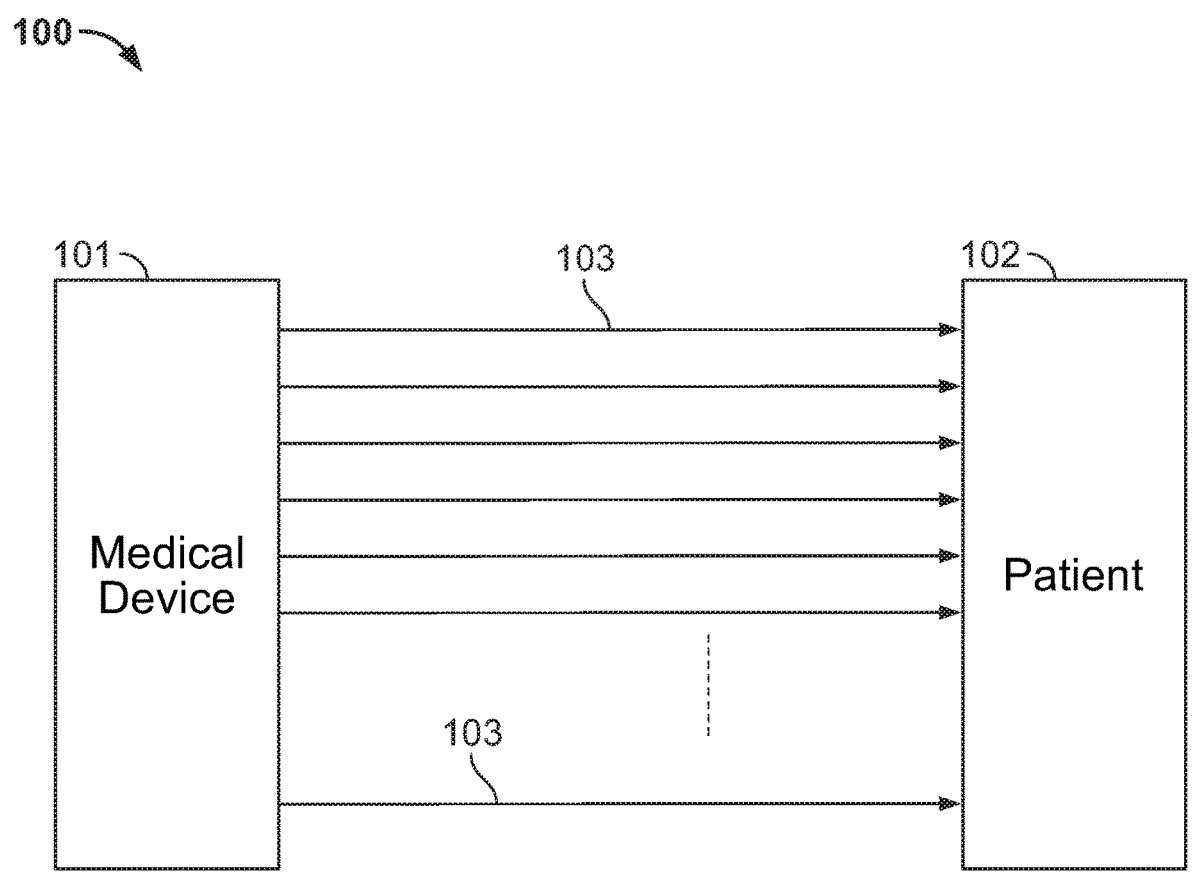
FIG. 1 shows a block diagram of a medical system comprising a large number of electrodes deployed on a patient body.

The term 'user' is used interchangeably to refer to a surgeon, neuro-physician, neuro-surgeon, neuro-physiologist, technician or operator of the EEG system and/or other patient-care personnel or staff.

A "computing device" is at least one of a cellular phone, PDA, smart phone, tablet computing device, patient monitor, custom kiosk, or other computing device capable of executing programmatic instructions. It should further be appreciated that each device and monitoring system may have wireless and wired receivers and transmitters capable of sending and transmitting data. Each "computing device" may be coupled to at least one display, which displays information about the patient parameters and the functioning of the system, by means of a GUI. The GUI also presents various menus that allow users to configure settings according to their requirements. The system further comprises at least one processor (not shown) to control the operation of the entire system and its components. It should further be appreciated that the at least one processor is capable of processing programmatic instructions, has a memory capable of storing programmatic instructions, and employs software comprised of a plurality of programmatic instructions for performing the processes described herein. In one embodiment, the at least one processor is a computing device capable of receiving, executing, and transmitting a plurality of programmatic instructions stored on a volatile or non-volatile computer readable medium. In addition, the software comprised of a plurality of programmatic instructions for performing the processes described herein may be implemented by a computer processor capable of processing programmatic instructions and a memory capable of storing programmatic instructions.

"Electrode" refers to a conductor used to establish electrical contact with a nonmetallic part of a circuit. EEG electrodes are small metal discs or cylinders usually made of stainless steel, tin, gold, platinum or silver covered with a silver chloride coating. They are typically placed on the scalp or in the body on predetermined locations.

The "integrity verification system (IVS)" consists of a hardware test fixture, hardware test circuitry and software diagnostics used to verify baseline operation for running tests. The purpose of these is to establish a definitive known environment and test sequence which will allow detecting fault conditions prior to using the equipment on an actual patient.

The term "impedance test" shall mean methods for verifying the correct functionality of the electrode impedance measurement capability of the EEG recording device, as further described herein.

The term "channel uniqueness test" shall mean methods for verifying that each channel of the EEG recording device is displaying data for that channel only and with the expected physical to graphical mapping, as further described herein. This test also verifies the correct functionality of the patient connection switches for each EEG recording device channel, as further described herein.

The term "test for verifying a state of a switch" shall mean methods for verifying the correct functionality of each high and low side stimulator switch within the switch matrix of the EEG recording device, as further described herein.

The term "test for verifying connector IDs" shall mean methods for verifying the correct functionality of the detection and communication capability of the EEG recording device with identification circuitry within electrode connections, as further described herein.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

In the description and claims of the application, each of the words "comprise" "include" and "have", and forms thereof, are not necessarily limited to members in a list with which the words may be associated. It should be noted herein that any feature or component described in association with a specific embodiment may be used and implemented with any other embodiment unless clearly indicated otherwise.

As used herein, the indefinite articles "a" and "an" mean "at least one" or "one or more" unless the context clearly dictates otherwise.

The present specification provides a hardware test fixture, associated hardware test circuitry, and software diagnostics that can be used with an EEG recording device, particularly for ECoG and sEEG monitoring and preferably with an integrated switch matrix, to test at least one functionality of the device before starting an EEG recording procedure.

FIG. 1 shows a block diagram of a conventional medical system 100 comprising a large number of electrodes positioned on the body of a patient 102. The medical device 101 represents any conventional neuromonitoring medical system which comprises a large number of electrodes, such as an EEG (electroencephalography) system, which is used for monitoring the neurological state of a patient for diagnosis and preventive treatment of certain diseases and for monitoring patients during anesthesia, among other procedures. As shown in FIG. 1, the medical device 101 is coupled to the patient 102 through a plurality of electrical leads 103 such that each of the leads 103 is coupled to an electrode (not shown) positioned at an appropriate location on the body of the patient. In applications that require a large number of electrodes to be coupled to the human body, the setup, placement and management of electrodes is a cumbersome process. As each electrode is positioned at a different location to capture the electrical activity in its vicinity, the input voltage recorded from each electrode has to be processed independently. Therefore, the system is required to maintain the identity of each of the electrical leads 103 and accordingly process the input received from it. After positioning any electrode at its required location on the body of the patient 102, the user is required to correctly connect the electrode lead 103 corresponding to each electrode to a specific input channel designated for that electrode in the medical device 101.

Figure 2:
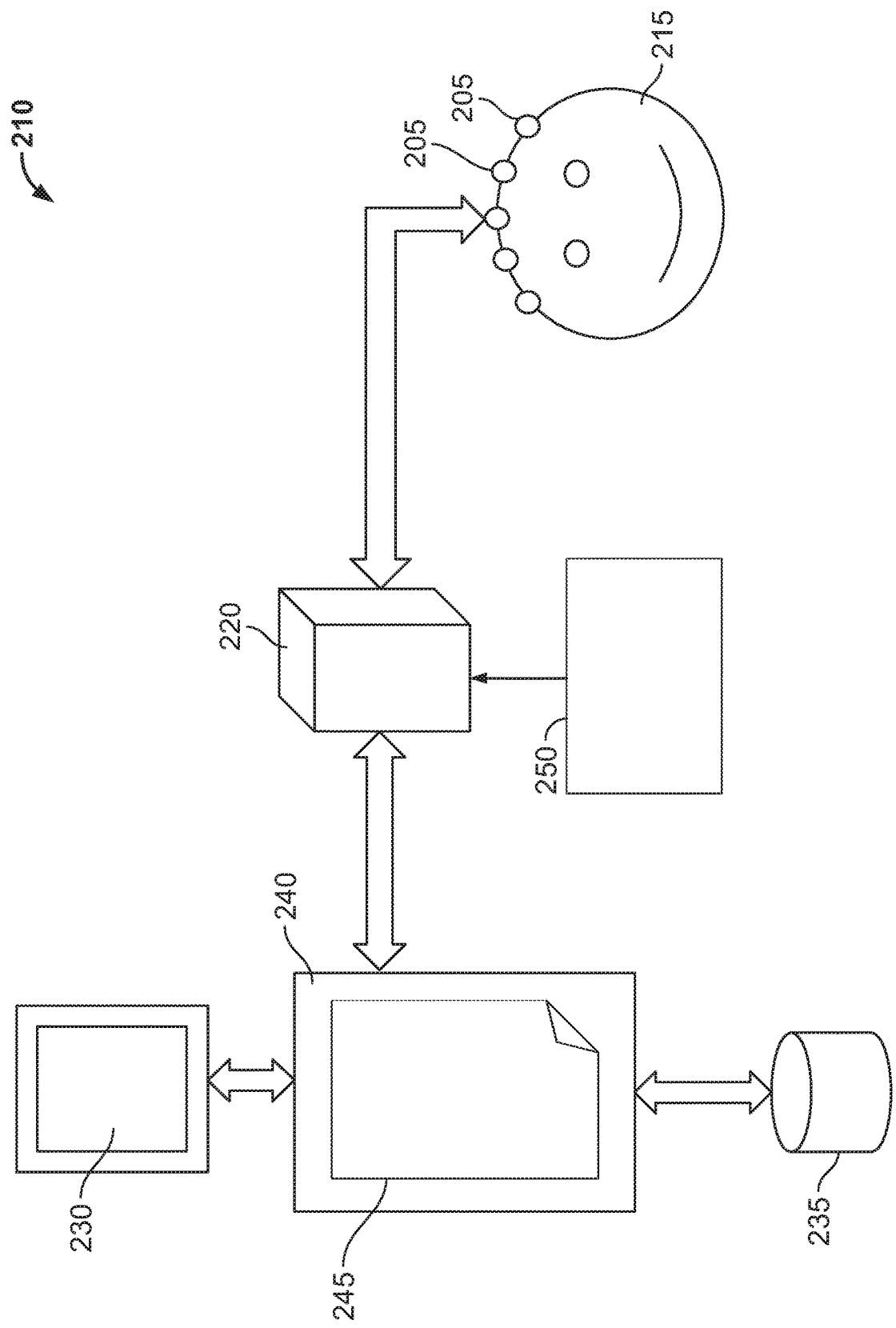
FIG. 2 illustrates an EEG system for detecting, diagnosing, or predicting neurological events from EEG signals, in accordance with some embodiments of the present specification.

FIG. 2 illustrates an EEG system 210 for detecting, diagnosing, or predicting neurological events from EEG signals, in accordance with some embodiments of the present specification. The figure shows a plurality of EEG sensors or electrodes 205 spatially positioned on a layer of tissue, such as the scalp of a patient 215, or intracranially on the surface of the brain as grid or strip electrodes or within the brain as depth electrodes. The plurality of electrodes 205 are connected to a multi-channel recording device 220 that is in data communication with a computing device 240. In an embodiment, the computing device 240 comprises a cortical stimulator 250 which is connected to the recording device for use with functional mapping. The computing device 240 is in data communication with a display unit 230 and at least one database 235.

In various embodiments, the plurality of electrodes 205 are small metal discs or cylinders typically made of stainless steel, tin, gold, platinum or silver covered with a silver chloride coating. In some embodiments, the plurality of electrodes 205 are placed on the scalp or in the body of patient 215. In another embodiment, electrodes 205 are placed as intracranial electrodes as a combination of one or more depth electrodes, grid electrodes, and strip electrodes. The plurality of electrodes 205 sense electrical signals (EEG signals) on the patient's brain and the analog signals enter the multi-channel recording device 220 that amplifies the signals, converts the signals from analog to digital, and communicates the resultant digital EEG signal to the computing device 240 over a communication link. Stimulus from the cortical stimulator 250 is routed into selected electrodes on the patient 215 via the integrated switch matrix within the recording device 220. In various embodiments, the cortical stimulator 250 is integrated within the recording device 220 or is an external device. In embodiments, the communication link between recording device 220 and computing device 240 may be a wired or wireless link.

The computing device 240 includes an input/output controller, at least one communications interface and system memory. The system memory includes at least one random access memory (RAM) and at least one read-only memory (ROM). These elements are in communication with a central processing unit (CPU) to enable operation of the computing device 240. In various embodiments, the computing device 240 may be a conventional standalone computer or alternatively, the functions of the computing device 240 may be distributed across multiple computer systems and architectures. For example, in a distributed architecture the at least one database 235 and processing circuitry are housed in separate units or locations. Some units perform primary processing functions and contain at a minimum a general controller or a processing circuitry and a system memory.

The computing device 240 executes EEG software 245 to process, store, retrieve and display, on the display unit 230, the patient's EEG data. In embodiments, the EEG software 245 processes the received signals, extracts parameters that characterize the EEG data, and generates a display of the data for a user. The processed EEG data is either displayed on the display unit 230 in real-time or stored in at least one database 235 for later analyses.

In some embodiments, execution of sequences of programmatic instructions enable or cause the CPU to perform various functions and processes. In alternate embodiments, hard-wired circuitry may be used in place of, or in combination with, software instructions for implementation of the processes of systems and methods described in this application. Thus, the systems and methods described are not limited to any specific combination of hardware and software.

Figure 3B:
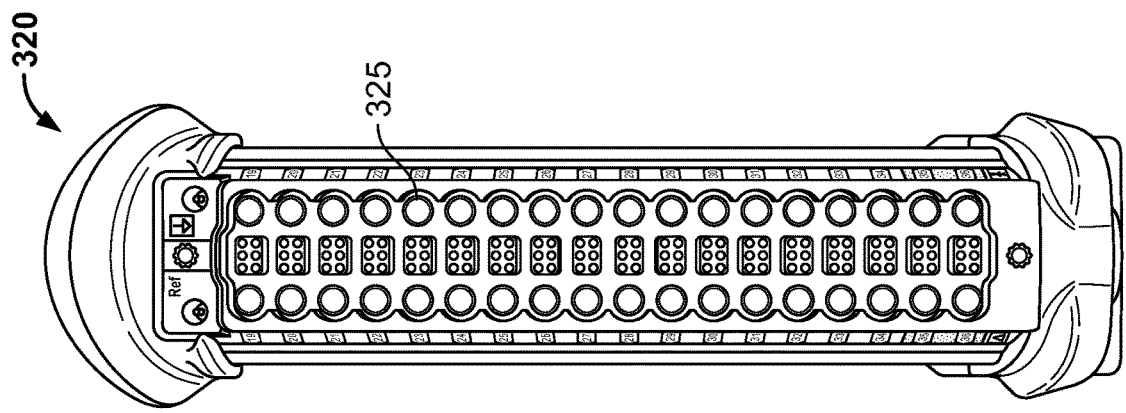
FIG. 3B is a side view of the multi-channel recording device of FIG. 3A.
Figure 3A:
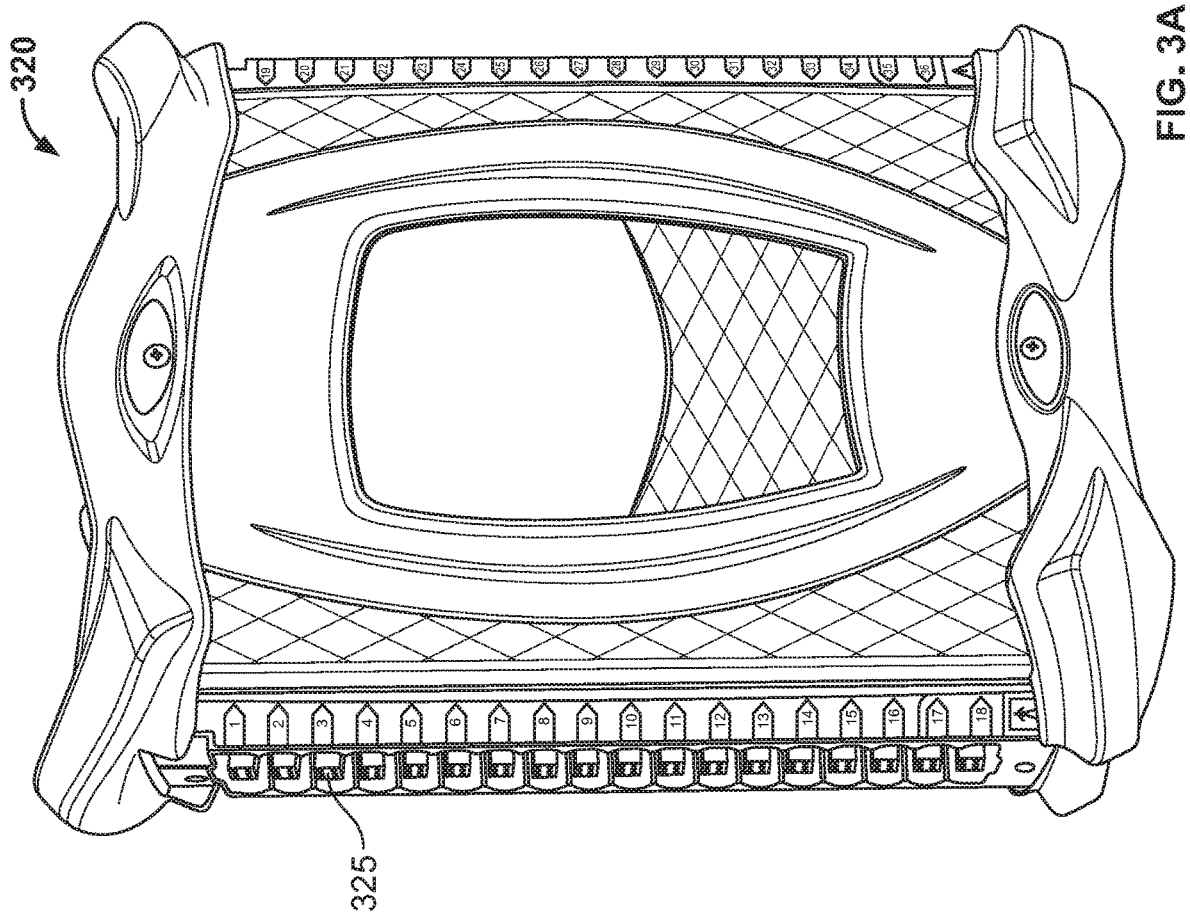
FIG. 3A is a perspective view of a multi-channel recording device, in accordance with an embodiment of the present specification.

FIGS. 3A and 3B show perspective and side views, respectively, of an exemplary multi-channel recording device 320, in accordance with some embodiments of the present specification. The multi-channel recording device 320 is configured for ECoG and sEEG monitoring. The recording device 320 has a plurality of electrode input channels or ports 325. In some embodiments, the recording device 320 is configured to record up to 576 channels at an 8 kHz sampling rate. In some embodiments, the recording device 320 includes an onboard battery and data storage to allow for patient mobility. In embodiments, the recording device 320 is configured so that a user may select any input as ground on any recording device and select any other input as the recording reference. Further, a user may create montages up to, and including, all electrodes with a single click on an associated graphical user interface (GUI). In some embodiments, the recording device 320 is configured to streamline electrode layout with automated input mapping. In some embodiments, referring back to FIG. 2, the EEG software 245 is configured to control integrated switch matrix stimulation. Additionally, in some embodiments, the software 245 allows a user to monitor multiple patients from one computer, control IP camera switching and functions, and simplify data review with trends and detection software. In some embodiments, all case settings, including montages, follow the patient record. In some embodiments, the software 245 includes a feature to automatically synchronize stimulus to response annotations.

Referring to FIGS. 2, 3A and 3B, in an embodiment, each of the plurality of electrodes 205 (FIG. 2) is grouped in a connector which has wired data communication with the corresponding input channel or port 325. Each connector corresponding to a plurality of electrodes is programmed with a unique identifier. Thus, each connector and its plurality of electrodes can be uniquely identified and located according to its placement within the range of input channels or ports 325. Consequently, each of the EEG signals acquired by the recording device 220 is uniquely identified with the associated electrode. The multi-channel recording device 320 of FIGS. 3A and 3B may be used in ECoG and sEEG systems to monitor, assess and map the brains of epilepsy patients who have may benefit from surgery and have not responded to less invasive treatments including pharmaceuticals.

An intracranial EEG procedure requires accurate information such as but not limited to electrode impedance values, and electrode contact viability from the EEG recording device being used. In embodiments where the EEG recording device includes an integrated switch matrix for an internal or external cortical stimulator, the respective ON/OFF states of the recording channel switches and stimulator switches must also be functional and correct to provide accurate EEG information to a physician. Further, for EEG data and stimulator routing, it is also imperative to ensure that the channel mapping from patient to a computer screen is accurate and that each channel is acting independently, before starting an EEG recording procedure.

The present specification provides an integrated verification system (IVS) which consists of a hardware test fixture, hardware test circuitry, and software diagnostics that can be used with an EEG recording device with integrated switch matrix to test the necessary functionality of the device before starting an EEG recording procedure. The IVS verifies a required functionality of the impedance measurement and electrode contact viability measurement within the EEG device. The IVS also verifies that each recording channel acts independently (channel uniqueness) and that the identification of unique identifiers in the electrode connections is functioning correctly. In embodiments, the IVS confirms that the recording channel and stimulator switches are functioning as expected. Hence, in various embodiments, the IVS ensures the EEG device is in working order before an EEG procedure begins.

Figure 4:
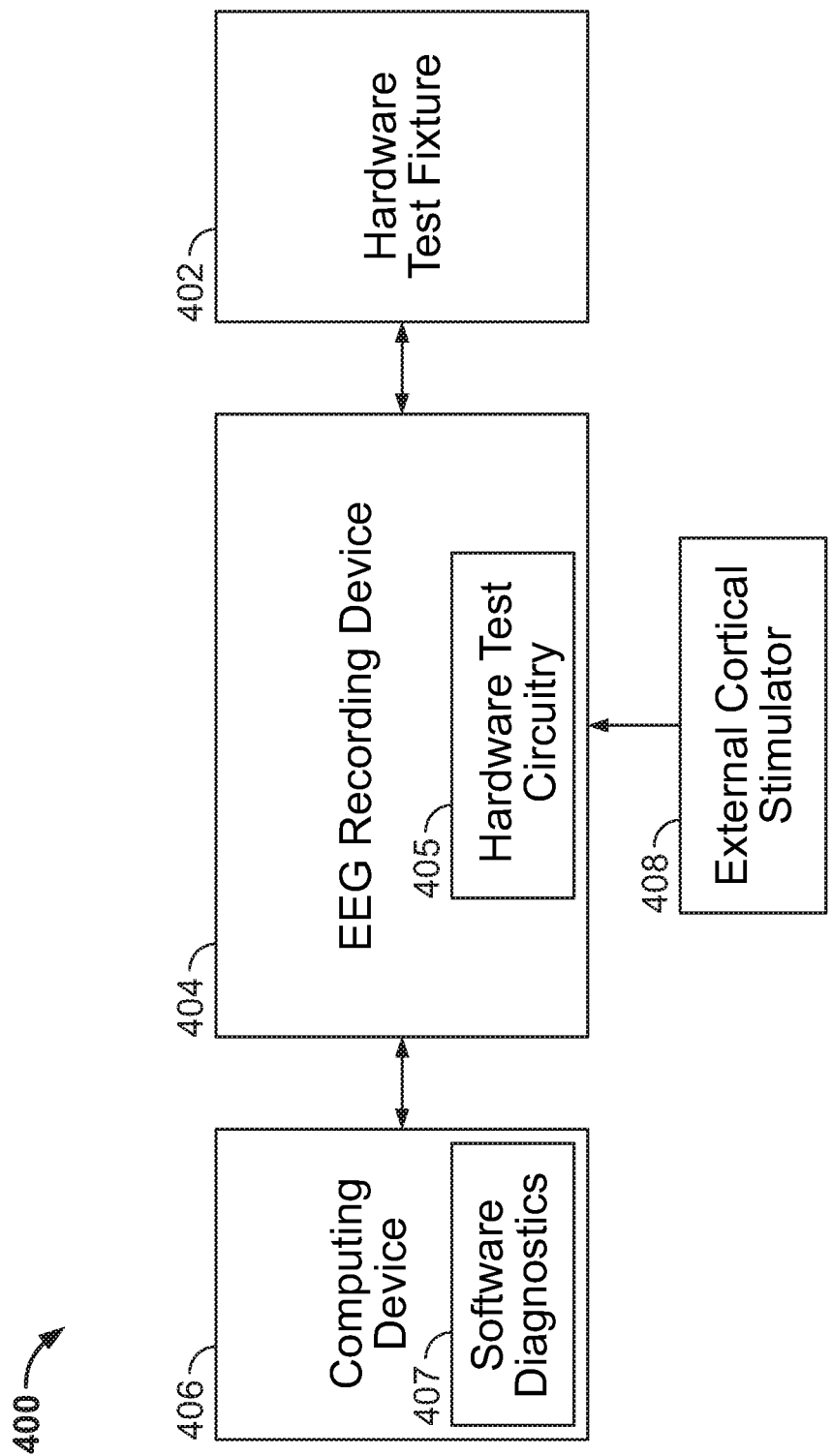
FIG. 4 is a block diagram illustrating a test fixture, coupled to an EEG recording device, used for testing a plurality of parameters of said device, in accordance with an embodiment of the present specification.

FIG. 4 is a block diagram illustrating an integrated verification system (IVS) 400 in accordance with some embodiments of the present specification. The IVS 400 consists of a hardware test fixture, or hardware testing device, 402 coupled with an EEG recording device 404, and its associated hardware test circuitry 405, which in turn is coupled with a computing device 406 with software diagnostics 407, for testing a plurality of parameters of said recording device, in accordance with an embodiment of the present specification. As shown, hardware test fixture 402 is coupled with the EEG recording device 404 for testing a plurality of pre-defined parameters of said device, which in turn is controlled by the computing device 406. In an embodiment, the EEG recording device 404 comprises a plurality of electrodes that record electrical signals (EEG signals) from a patient's brain and communicate the signals to the computing device 406 over a communication link. The computing device 406 executes diagnostic EEG software to test a plurality of predefined EEG data parameters. In an embodiment, the hardware test fixture 402 comprises individual resistors corresponding to each electrode channel input of the EEG device, patient ground, and common reference. These resistors are connected at a common node on the fixture. Impedance measurement is implemented by injecting a known current through each channel input through the test fixture resistors to a common node. The current flows from that common node through a known resistance value to the recording device ground or midpoint voltage bias. The voltage produced over each resistor is sensed by the EEG recording device 404 and can be used to calculate the value of that resistor. The common node allows every channel input to be measured in the same way without changing configuration.

In embodiments, the recording device 404 can measure impedances from nominally 0 Ohm to some maximum value with some expected measurement error. The hardware test fixture 402 presents resistor values to each channel input that are less than the maximum measurable value. When the impedance measurement test is run, each measured channel resistance is verified to be within the expected measurement error of the resistor value for the corresponding test fixture input.

In an embodiment, the test fixture 402 further comprises a uniquely programmed identification circuit for each group of inputs on the EEG recording device 404. An identification circuit simulates a number of different electrode connectors provided at a side of the recording device 404 at the same time. Each identification circuit in the test fixture 402 is programmed with a unique value, corresponding to a location of the connectors. In embodiments, at least one of these identification circuits has a reverse polarity. This requires the recording device 404 to communicate in reverse polarity mode with said identification circuit for verifying that the recording device 404 is functioning correctly and can communicate in either normal or reverse polarity. In order to verify that the detection and mapping of connectors on the EEG recording device 404 is functioning as required, communication is established between each of the unique identification circuits and the corresponding groups of connectors and the different positions of each of the connectors is verified by the software diagnostics 407.

Examples of the parameters that are tested/verified by the software diagnostics 407 comprise impedance measurement of EEG electrodes, channel uniqueness of each EEG channel, electrode contact viability detection, both recording channel and stimulator switch ON/OFF states, and correct identification of all connectors of the EEG electrodes.

In an embodiment, one hardware test fixture 402 is connected to the EEG recording device 404, internal hardware test circuitry 405 is activated as needed, and software diagnostics are run to complete the parameter testing. Alternatively, if the EEG recording device's 404 electrode channel count requires more than one test fixture, in embodiments, more than one of the identical hardware test fixtures 402 may be connected to the EEG recording device 404. In another embodiment, an external stimulator 408 is used to test the stimulator switch ON/OFF states. The external cortical stimulator 408 is used for functional mapping during a procedure. In various embodiments, either an internal constant voltage stimulator or an external cortical stimulator 408 is used to verify the switch functionality as a part of the IVS 400. One advantage of using the external cortical stimulator 408 is that voltage and current compliance through the recording device and integrated switch matrix can be verified with the actual pulse parameters used for cortical stimulation. The diagnostic software 407 controls the hardware setup of the test hardware circuitry 405 and processes acquired data to verify test results.

Figure 5:
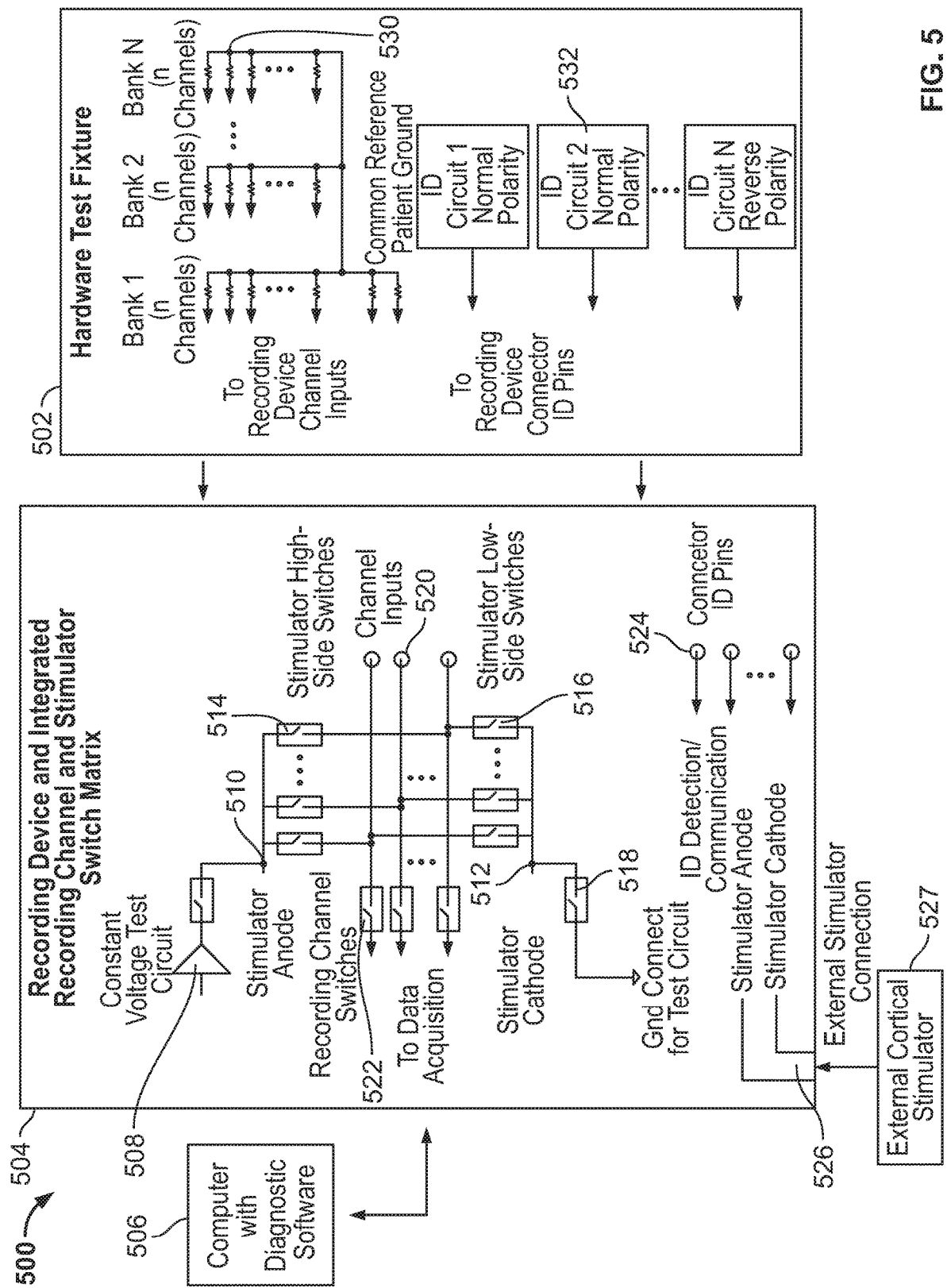
FIG. 5 is a circuit diagram illustrating a hardware test fixture, coupled with an EEG recording device, associated hardware test circuitry and computer, and associated software diagnostics, used for testing a plurality of parameters of said device, in accordance with an embodiment of the present specification.

FIG. 5 is a circuit diagram illustrating an IVS 500 which consists of a hardware test fixture 502 coupled with an EEG recording device 504 and associated hardware test circuitry and a computing device 506 with software diagnostics for testing a plurality of parameters of said recording device, in accordance with an embodiment of the present specification. As shown, hardware test fixture 502 is coupled with an EEG recording device 504 for testing a plurality of pre-defined parameters (for example, impedance measurement, channel uniqueness, switch functionality, and identification of unique identifiers in electrode connections) of said device, which in turn is controlled by a computing device 506. In an embodiment, the EEG recording device 504 comprises a plurality of electrodes that record electrical signals (EEG signals) from a patient's brain and communicate the signals to the computing device 506 over a communication link. The computing device 506 executes diagnostic EEG software to test a plurality of predefined EEG data parameters. In the circuit diagram shown in FIG. 5, the EEG recording device 504 comprises a constant voltage test circuit or stimulator 508, a stimulator anode 510, a stimulator cathode 512, a plurality of stimulator high side switches 514, a plurality of stimulator low side switches 516, a ground connect 518 for the constant voltage test circuit 508, EEG electrode channel connectors 520 and corresponding recording channel switches 522. The EEG recording device 504 also comprises a plurality of connector identification pins 524 and external stimulator connector 526. In embodiments, the stimulator anode 510 is used as a connection point for a test stimulator to connect to a selected stimulator switch connection. In embodiments, the stimulator cathode 512 is used as a return for the current produced by the test stimulator through the selected stimulation switch connection, i.e. one high side and one low side switch connected. In embodiments, the stimulator anode 510 and stimulator cathode 512 comprise separate entities to allow either the constant voltage test circuit 508 or the external cortical stimulator 527 to be used as the test stimulator. The high side switches 514 and low side switches 516 are used to route a test stimulus to a given pair of electrode connections. In various embodiments, only one of either the constant voltage test circuit 508 or external cortical stimulator 527 will be connected to the stimulator anode 510 and stimulator cathode 520 at one time. The constant voltage test circuit can be connected to the stimulator anode and cathode for testing the stimulator switch ON/OFF states. Alternatively, the constant voltage test circuit can be disconnected from the stimulator anode and cathode and the external stimulator can be connected for testing the stimulator switch ON/OFF states.

In an embodiment, the test fixture 502 comprises individual resistors 530 corresponding to each electrode channel input of the EEG device, patient ground, and common reference. The resistors 530 are arranged in groups (banks) for connecting with EEG device channel inputs and are connected at a common node on the fixture 502. The fixture 502 also comprises a plurality of uniquely programmed identification circuits 532 for connecting with the EEG device connector identification pins.

Figure 6:
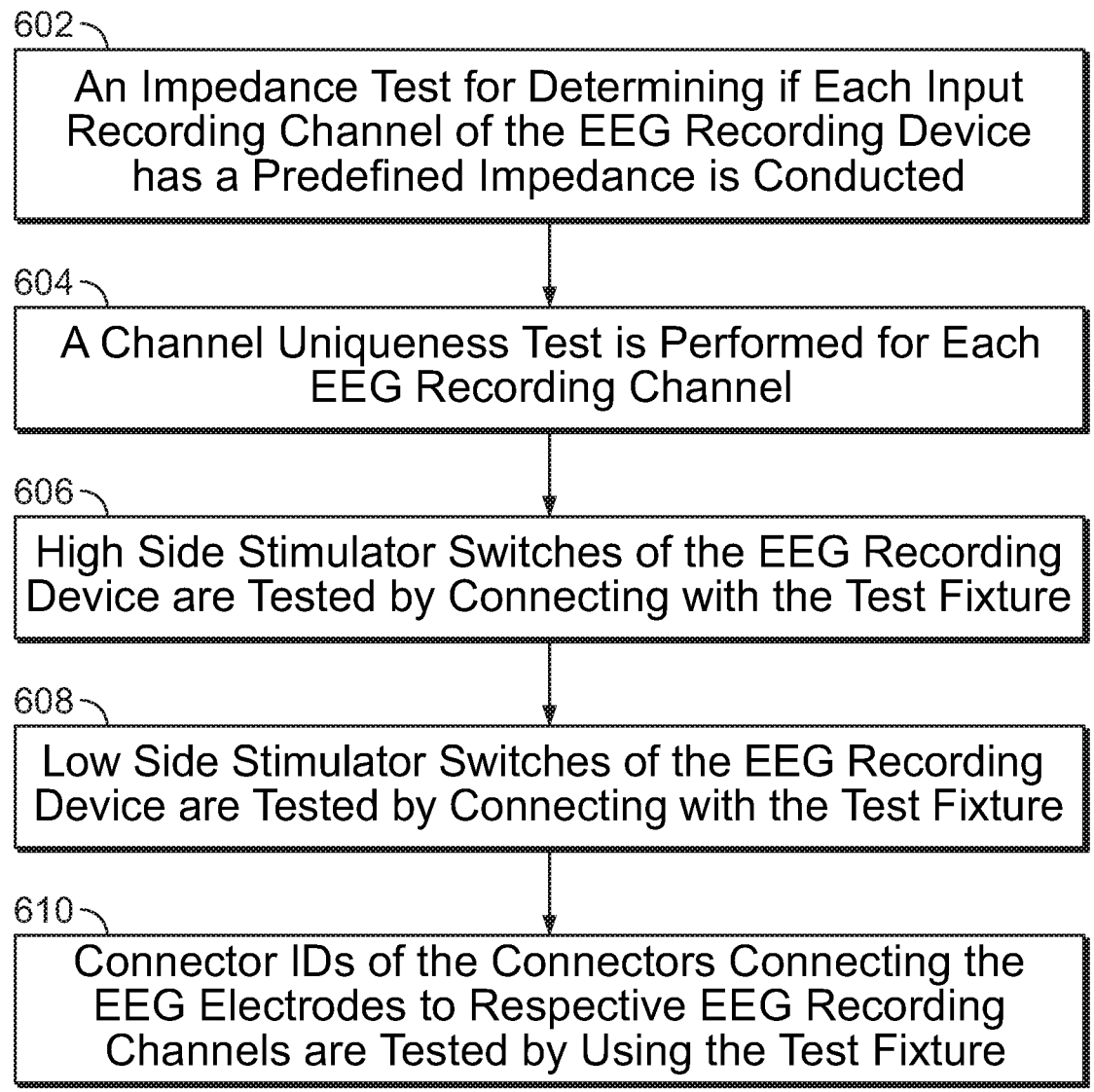
FIG. 6 is a flowchart illustrating the steps of diagnostic testing of a EEG recording device performed by using the hardware test fixture, associated hardware test circuitry, and software diagnostics as shown in FIG. 5.
Figure 7:
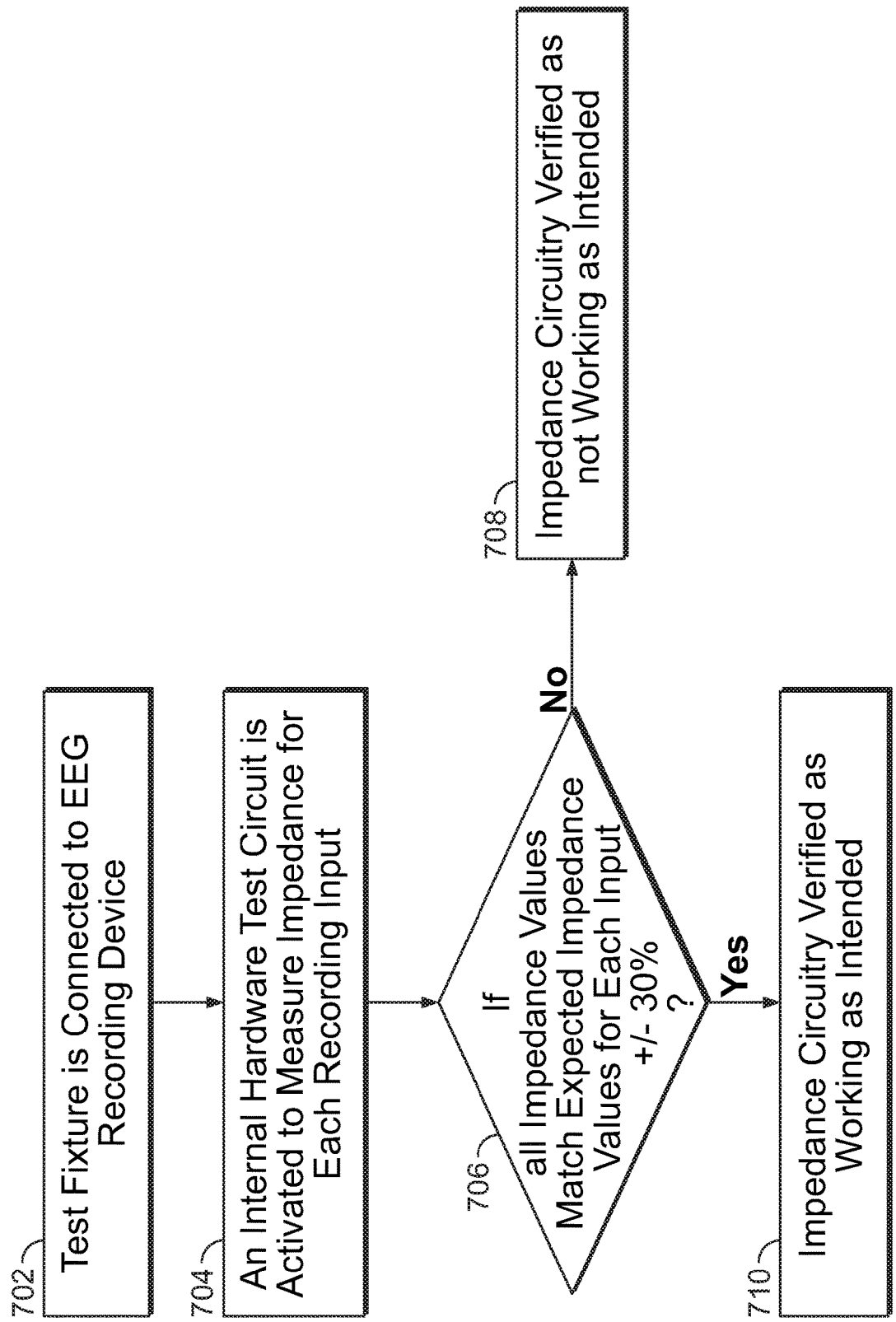
FIG. 7 is a flowchart illustrating the steps of testing impedance with an EEG recording device by using a test fixture, in accordance with an embodiment of the present specification.

FIG. 6 is a flowchart illustrating the steps of diagnostic testing of an EEG recording device performed by using the test fixture shown in FIG. 5. At step 602 an impedance test for determining if each input recording channel of the EEG recording device measures at a predefined impedance is conducted. FIG. 7 is a flowchart illustrating the steps of testing impedance with an EEG recording device by using a test fixture, in accordance with an embodiment of the present specification. At step 702, a test fixture is connected to the EEG recording device. An internal hardware test circuit is activated to measure impedance for each input recording channel of the EEG recording device at step 704. At step 706 it is determined if all impedance values match expected impedance values for each input while allowing for a measurement error margin of +/−30% of the expected impedance value. In some embodiments, the expected impedance value ranges from 499 Ohms to 49.9 kOhms. If all impedance values do not match expected impedance values for each input in a range of +/−30% of the expected impedance value, the impedance circuitry is verified as not working as intended at step 708. If all impedance values do match expected impedance values for each input in a range of +/−30% of the expected impedance value, the impedance circuitry is verified as working at step 710.

In an embodiment, the test fixture applies a sequence of resistance values within a range of 499 ohms to 49.9K ohms, one for each EEG channel input, patient ground, and common reference. Since the EEG recording device is physically arranged in banks of n channels, the resistors in the test fixture sequentially increase through n+1 unique values so that each adjacent bank of EEG recording channels has a unique set of resistor values. This reduces the likelihood of error when correlating test results with each bank of EEG recording channels. In an embodiment, for an EEG recording device comprising 8 EEG recording channels, each bank of channels has a unique sequence of values. For example, with reference to FIG. 5, bank 1 of hardware test fixture 502 may be associated with value 1, value 2, . . . value 8. Bank 2 may be associated with value 9, value 1, . . . value 7 etc. Each bank (such as the banks of hardware test fixture 502) corresponds to an individual ADC IC. When the software parses out data from an individual ADC IC, the sequence of values are unique when compared to any other ADC in the group. This makes it easier to differentiate between the data from two separate ADCs. In embodiments, the resistor values are spaced far enough to allow for expected error in impedance measurement. In some embodiments, the span between resistor values exceeds the expected measurement error margin of the impedance measurements. For example, in an embodiment, an expected measurement error margin is +/−30% and the impedance value of the resistors are spaced+/−40% apart from each other so that the spacing of the resistor values exceeds the measurement error margin.

In various embodiments, any shorted channels within a bank of a hardware test fixture are detectable when testing the impedance of each channel. For example, in some embodiments, if a channel 1 of a bank 1 of a test fixture has a low resistance value and a channel 2 of the bank 1 has a high resistance value and these 2 channels are shorted together, the short may not be detected when measuring channel 1 impedance as the low resistance in parallel with high resistance may be within the expected tolerance of the low resistance value. However, when channel 2 impedance is measured, the parallel resistance will be well out of tolerance from the expected high resistance value and a short will be detected. Since, all resistor values used on the test fixture fall within the measurement range of the recording device, a failed open input will also be detected. A diagnostic software running on a computing device coupled with the test fixture and the EEG recording device verifies expected impedance on each EEG recording channel.

Figure 8:
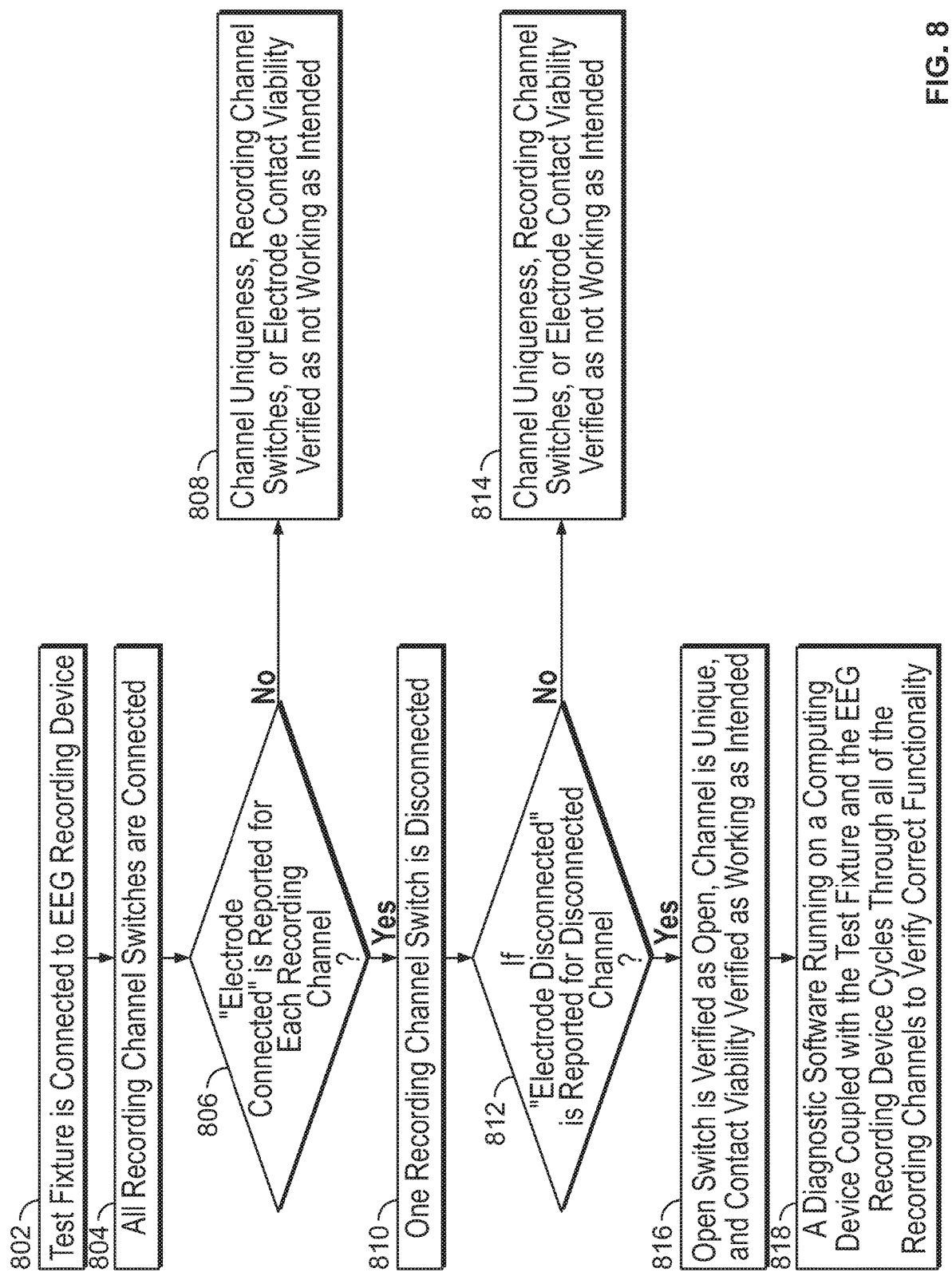
FIG. 8 is a flowchart illustrating the steps of testing channel uniqueness of an EEG recording device by using a test fixture, in accordance with an embodiment of the present specification.

Referring back to FIG. 6, at step 604 a channel uniqueness test is performed for each EEG recording channel. FIG. 8 is a flowchart illustrating the steps of testing channel uniqueness of an EEG recording device by using a test fixture, in accordance with an embodiment of the present specification. At step 802 a text fixture is connected to the EEG recording device. A plurality of resistors of the text fixture is connected to a plurality of EEG electrode recording channels. All recording channel switches are connected at step 804. At step 806, it is determined if a status of "electrode connected" is reported for each recording channel. If a status of "electrode connected" is not reported for each recording channel, channel uniqueness, recording channel switches, or electrode contact viability is verified as not working as intended at step 808. If a status of "electrode connected" is reported for each recording channel, one recording channel is disconnected at step 810. The EEG electrode recording channel is disconnected from the plurality of resistors of the text fixture. Then, at step 812, it is determined if a status of "electrode disconnected" is reported for the disconnected channel. If a status of "electrode disconnected" is not reported for the disconnected channel, channel uniqueness, recording channel switches, or electrode contact viability is verified as not working as intended at step 814. If a status of "electrode disconnected" is reported for the disconnected channel, an open switch is verified as open, the channel is unique, and contact viability is verified as working as intended at step 816. At step 818, a diagnostic software running on a computing device coupled with the test fixture and the EEG recording device cycles through all of the recording channels to verify the functionality of said channels.

In some embodiments, the channel uniqueness test combines a functional test of the recording channel switch ON/OFF states with a functional test of the electrode contact viability measurement. The test verifies 3 functions: 1) the recording channel switch "closed" and "open" functionality; 2) whether the "lead-off" function is working for that channel; and, 3) when an "electrode-disconnected" state is detected for that specific channel it is confirmed that the channel with the "electrode-disconnected" state matches the channel where the recording channel switch is opened, verifying channel uniqueness. The "lead-off" detection will flag an "electrode-disconnected" state if the resistance on the input is above a predefined minimum resistance from device ground. This minimum "electrode-disconnected" resistance value is above any resistor value used on the test fixture. This ensures that an "electrode-disconnected" state will not be detected if the recording channel is connected to the test fixture. The resistor values in the hardware test fixture are chosen to be below the minimum value of resistance required to generate an "electrode disconnected" state from the electrode contact viability measurement. This guarantees every channel connected to its corresponding test fixture resistor will produce an "electrode connected" state. For this test, the recording channel switches are opened one at a time with the test fixture connected. The diagnostic software confirms an "electrode disconnected" state on the EEG recording channel having an open switch. All other EEG recording channels having closed switches convey an "electrode connected" state. This test is repeated for each individual EEG recording channels. By verifying that the selected channel for an open switch matches the channel with an "electrode disconnected" state, channel uniqueness is confirmed. This test also verifies that the recording channel switches and electrode contact viability measurement are functioning as expected.

Figure 9:
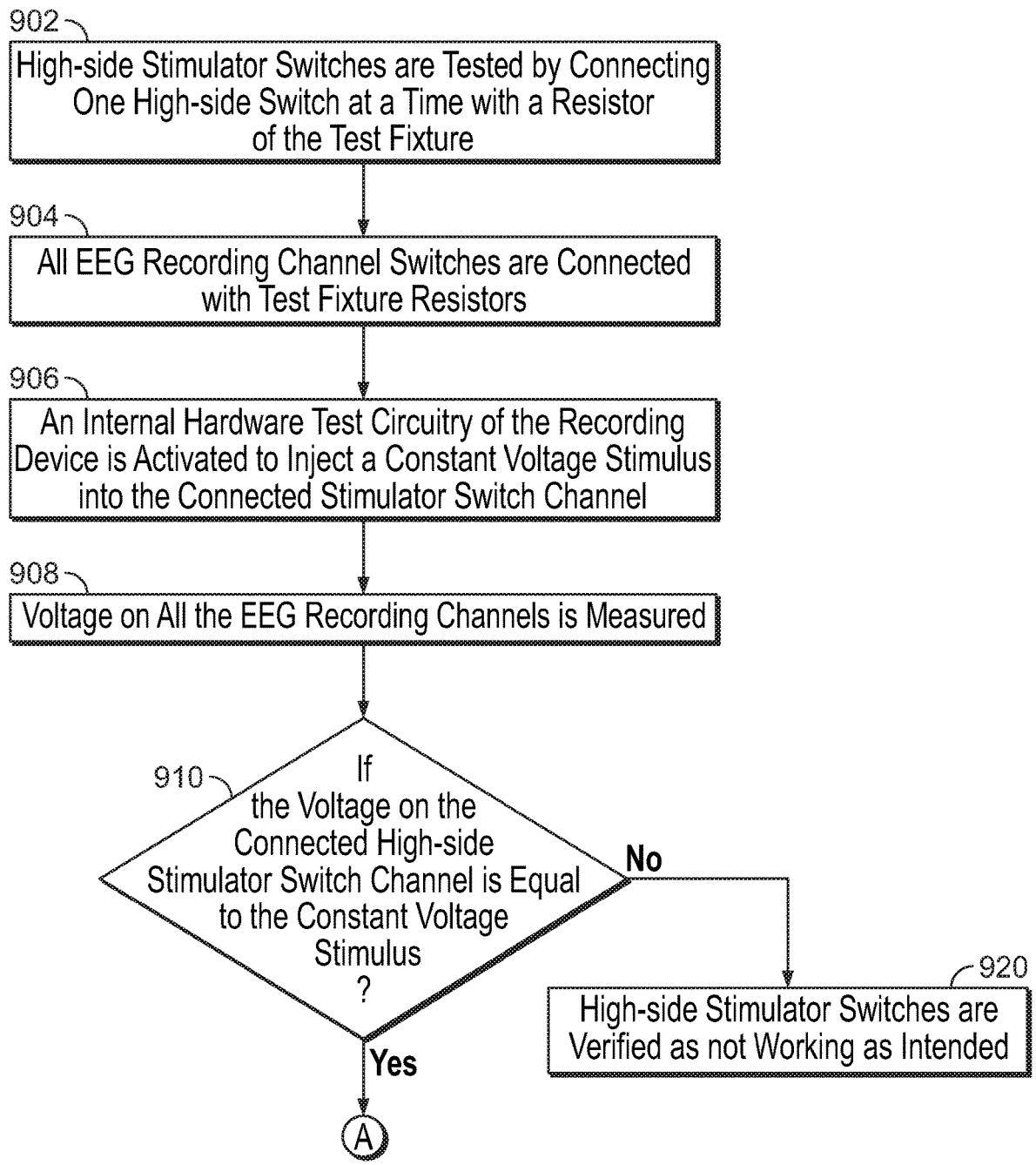
FIG. 9 is a flowchart illustrating the steps of testing high side stimulator switches of a EEG recording device by using a hardware test fixture, associated hardware test circuitry, and software diagnostics such as that described in the present specification, in accordance with an embodiment.
Figure 9:
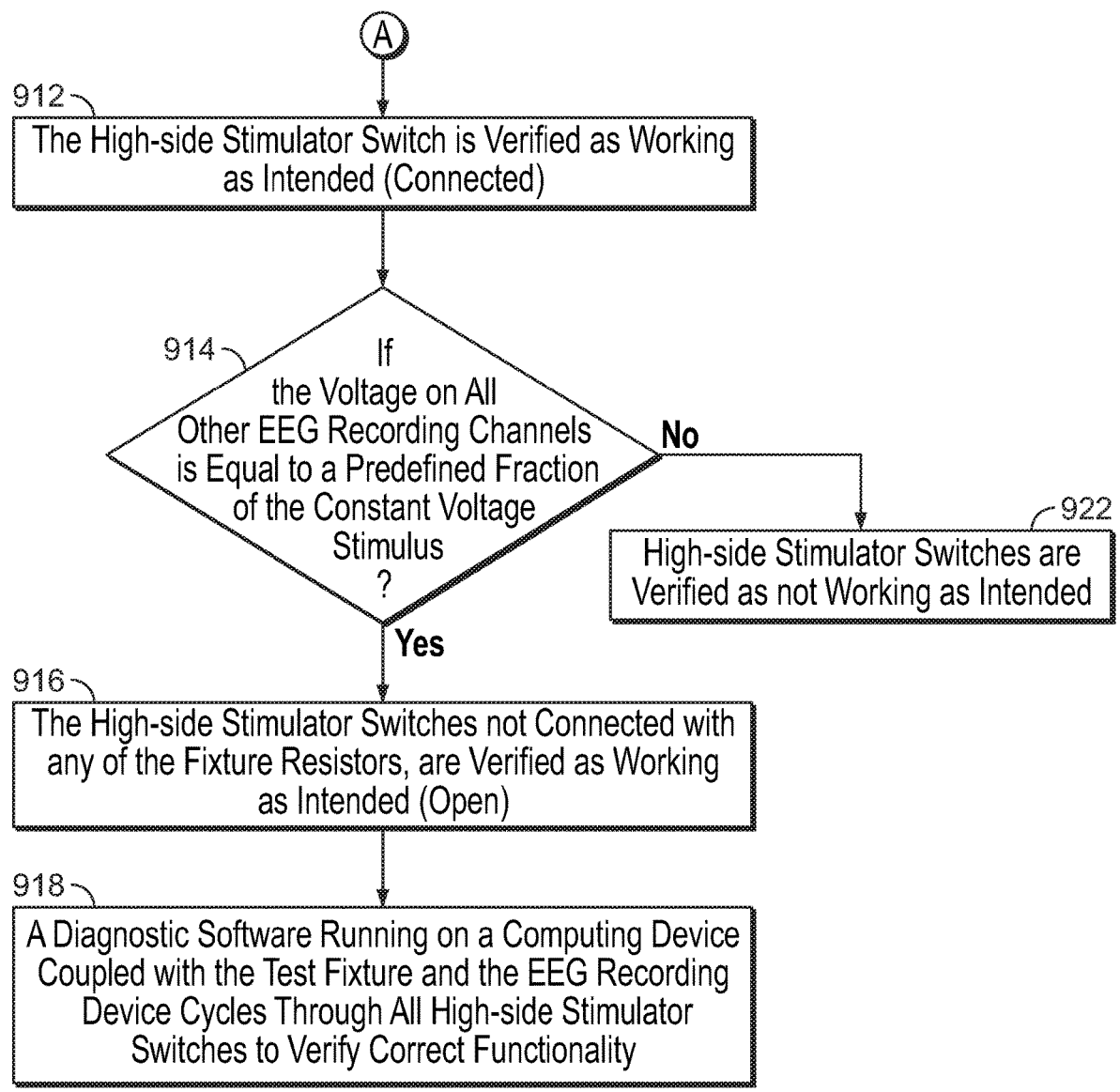

Referring back to FIG. 6, at step 606 high side stimulator switches of the EEG recording device are tested by connecting said switches with the test fixture. FIG. 9 is a flowchart illustrating the steps of testing high side stimulator switches of an EEG recording device by using the test fixture, in accordance with an embodiment of the present specification. In an embodiment, at step 902, the high-side stimulator switches are tested by connecting one high-side switch at a time with a resistor of the test fixture. At step 904 all EEG recording channel switches are connected with test fixture resistors. Next, in one embodiment, at step 906 an internal hardware test circuitry within the recording device is activated to inject a constant voltage stimulus into the connected stimulator switch channel. At step 908 the voltage on all the EEG recording channels is measured. At step 910 it is determined if the voltage on the connected high-side stimulator switch channel is equal to the constant voltage stimulus. At step 912 if the voltage on the connected high-side stimulator switch channel is equal to the constant voltage stimulus, the high-side stimulator switch is verified as working as intended (connected). At step 914 it is determined if the voltage on all EEG recording channels is equal to a predefined fraction of the constant voltage stimulus. In some embodiments, a constant voltage pulse generator produces a low voltage pulse in the mV range. If a channel with a high side switch measures this voltage value +/− some expected error, the high side switch for that channel is considered to be working. In embodiments, the other channels will be at a fraction of that voltage, 1/10 for example. If all other channels measure 1/10 of the pulse voltage value +/− some expected error, the high side switches for these channels will be considered to be working. This predefined fraction depends on the value of a resistance divider being applied to the signal in the channel being tested. At step 916 if the voltage on all other recording channels is equal to a predefined fraction of the constant voltage stimulus, the high-side stimulator switches not connected with any of the fixture resistor, are verified as working as intended (open). If the conditions of step 910 and 914 are not met, the corresponding high-side stimulator switches are verified as not working as intended, at steps 920 and 922 respectively. At step 918 a diagnostic software running on a computing device coupled with the test fixture and the EEG recording device cycles through all high-side stimulator switches to verify a required functionality.

Figure 10:
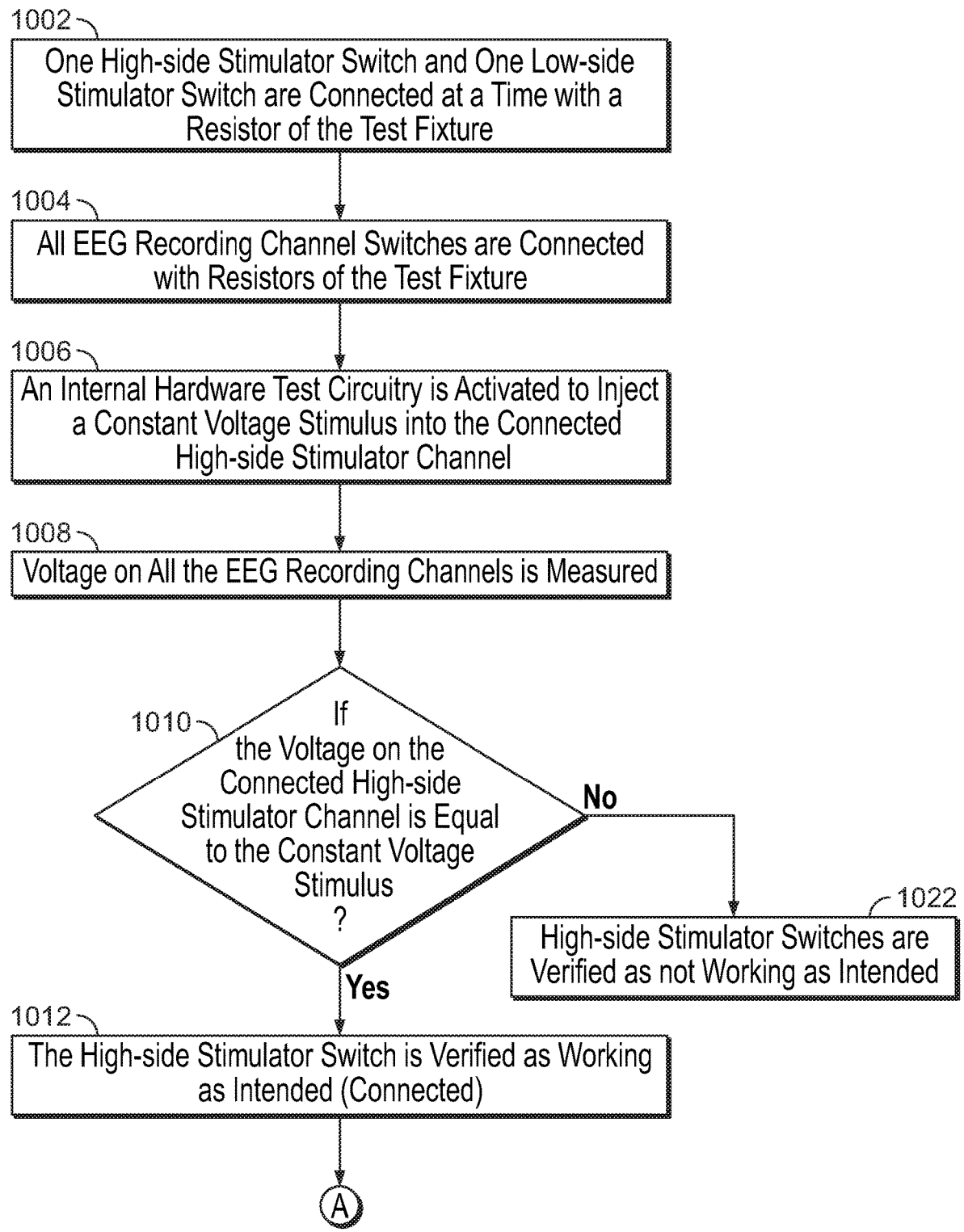
FIG. 10 is a flowchart illustrating the steps of testing low side stimulator switches of a EEG recording device by using a hardware test fixture, associated hardware test circuitry, and software diagnostics such as that described in the present specification, in accordance with an embodiment.
Figure 10:
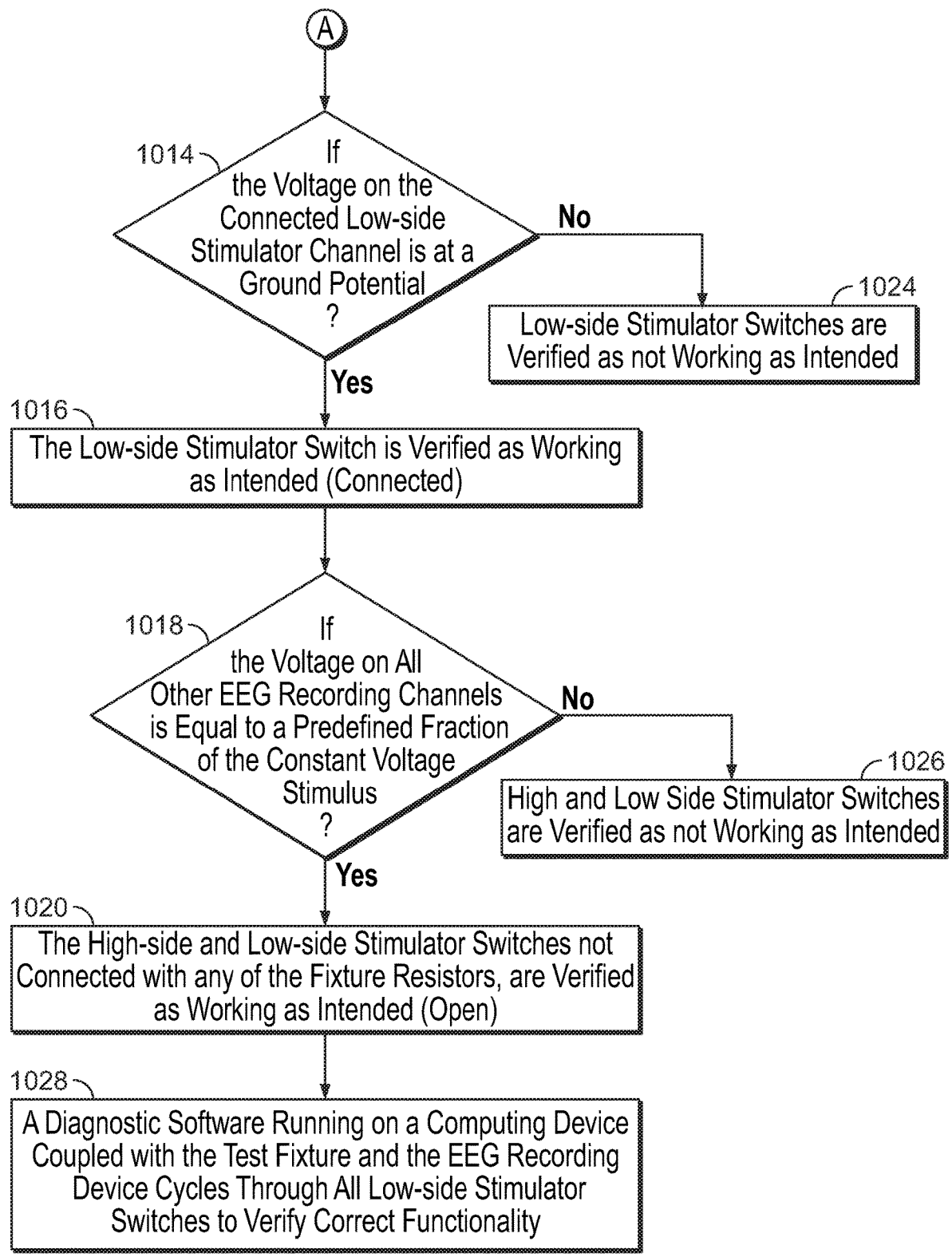

Referring back to FIG. 6, at step 608 low side stimulator switches of the EEG recording device are tested by connecting with the test fixture. FIG. 10 is a flowchart illustrating the steps of testing low side stimulator switches of an EEG recording device by using the test fixture, in accordance with an embodiment of the present specification. At step 1002, one high-side stimulator switch and one low-side stimulator switch are connected at a time with a resistor of the test fixture. At step 1004, all EEG recording channel switches are connected with a resistor of the test fixture. At step 1006, an internal hardware test circuitry is activated to inject a constant voltage stimulus into the connected high-side stimulator channel. At step 1008 the voltage on all the connected EEG recording channels is measured. In embodiments, during testing, a test stimulator current travels from the high side switch connection/channel input through one fixture resistor to a common node in the fixture, through a second fixture resistor to the channel input with the low side switch connection, and to ground. At step 1010 it is determined if the voltage on the connected high-side stimulator channel is equal to the constant voltage stimulus. At step 1012 if the voltage on the connected high-side stimulator channel is equal to the constant voltage stimulus, the high-side stimulator switch is verified as working as intended (connected). At step 1014 it is determined if the voltage on the connected low-side stimulator channel is at a ground potential. At step 1016 if the voltage on the connected low-side stimulator channel is at a ground potential, the low-side stimulator switch is verified as working as intended (connected). At step 1018 it is determined if the voltage on all EEG recording channels is equal to a predefined fraction of the constant voltage stimulus. In some embodiments, the predefined fraction is at least 1/10. At step 1020 if the voltage on all other recording channels is equal to a predefined fraction of the constant voltage stimulus, the high-side and low side stimulator switches not connected with any of the fixture resistor, are verified as working as intended (open). If the conditions of step 1010, 1014 and 1018 are not met, the corresponding high and/or low-side stimulator switches are verified as not working as intended, at steps 1022, 1024 and 1026 respectively. At step 1028 a diagnostic software running on a computing device coupled with the test fixture and the EEG recording device cycles through all low-side stimulator switches to verify a required functionality.

In an embodiment, the working states of the stimulator switches may be tested by firing a constant current pulse instead of a constant voltage pulse. This constant current pulse can be generated by the internal hardware test circuitry or by an external stimulator which is connected to the Stimulator Anode and Stimulator Cathode connections of the test fixture. Voltage measurement from EEG recording channels and the diagnostic software are used to determine if the said switches are functioning as expected.

Figure 11:
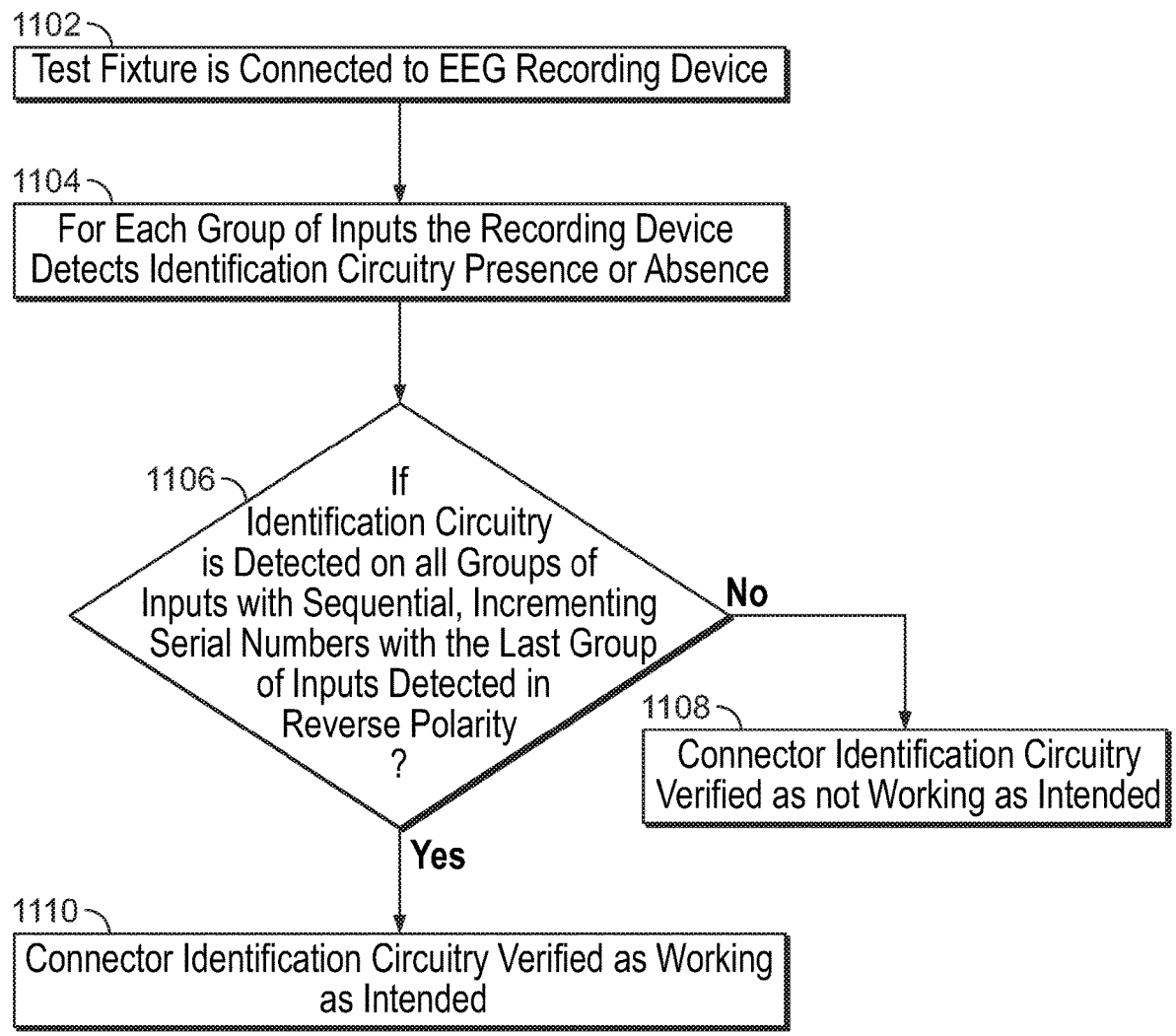
FIG. 11 is a flowchart illustrating the steps of verifying connector IDs of an EEG recording device by using a test fixture, in accordance with an embodiment of the present specification.

Referring back to FIG. 6, at step 610 connector identification of the connectors connecting the EEG electrodes to respective EEG recording channels are tested by using the hardware test fixture. FIG. 11 is a flowchart illustrating the steps of verifying connector IDs of an EEG recording device by using a test fixture, in accordance with an embodiment of the present specification. At step 1102 a test fixture is connected to the EEG recording device. For each group of inputs, the recording device detects the presence or absence of identification circuitry at step 1104. In various embodiments, the identification circuitry is a part of the test fixture and is identical to identification circuitry that would be in an actual electrode connector. The test process verifies that the identification detection and communication functionality of the EEG recording devices is working on all connection ports. Polarity detection is a part of the capability of this function as the electrode connectors could be oriented in different directions on the EEG recording device connection ports. Identification circuitry is described with reference to FIG. 5. At step 1106, it is determined if identification circuitry is detected on all groups of inputs with sequential, incrementing serial numbers with the last group of inputs detected in reverse polarity. If identification circuitry is not detected on all groups of inputs with sequential, incrementing serial numbers with the last group of inputs detected in reverse polarity, the connector identification circuitry is verified as not working as intended at step 1108. If identification circuitry is detected on all groups of inputs with sequential, incrementing serial numbers with the last group of inputs detected in reverse polarity, the connector identification circuitry is verified as working as intended at step 1110. In embodiments, the test fixture comprises identification circuitry equivalent to that used in actual patient electrode connectors. Each group of adjacent EEG recording channels has its own unique value programmed into the test fixture identification circuitry. In various embodiments, a predefined number of groups of adjacent EEG recording channels are provided for each recording device and at least one ID group is provided per predefined number of channels. For example, in an embodiment, there are 18 groups of inputs recording channels for each side of the recording device, wherein each group has 4 recording channels. At least one of the identification circuits on the test fixture is reverse polarized, as described above, to exercise reversible connection identification in the recording device. The test fixture is connected to the recording device and all connectors are scanned. The diagnostic software verifies expected values for all recording device ID connections and correct addressing of acquired ID values. In embodiments, the test fixture can only be applied to the EEG recording device in one position or orientation, meaning a unique serial number programmed into each ID circuitry block must correspond with the expected serial number for that location. If all the serial numbers are correct, correct addressing is verified.

The above examples are merely illustrative of the many applications of the system and method of present specification. Although only a few embodiments of the present specification have been described herein, it should be understood that the present specification might be embodied in many other specific forms without departing from the spirit or scope of the specification. Therefore, the present examples and embodiments are to be considered as illustrative and not restrictive, and the specification may be modified within the scope of the appended claims.

We claim:

1. A method of performing a diagnostic test on an electroencephalography (EEG) recording device, wherein the EEG recording device comprises at least one stimulator coupled with a plurality of EEG electrode recording channels and recording channel connectors connecting one or more EEG electrodes to the plurality of EEG electrode recording channels and wherein the diagnostic test is performed by a hardware testing device comprising a plurality of resistors coupled with one or more of the plurality of EEG recording channels and corresponding recording channel connectors, the method comprising:
   performing an impedance test to determine if each EEG recording channel of the plurality of EEG electrode recording channels has a predefined impedance;
   performing a channel uniqueness test on each EEG recording channel of the plurality of EEG electrode recording channels;
   performing a test to verify a state of a switch of the at least one stimulator of the EEG recording device; and
   performing a test to verify a correct functionality for each of the electrode connections.

2. The method of claim 1, wherein the at least one stimulator comprises ha a constant voltage test stimulator.

3. The method of claim 2, wherein the constant voltage test stimulator comprises a stimulator anode adapted to connect to high side switches of the at least one stimulator, a stimulator cathode adapted to connect to the low side switches of the at least one stimulator, and a ground connect.

4. The method of claim 3, wherein performing a test adapted to verify the state of the switch of the stimulator of the EEG recording device comprises performing a test adapted to verify a state of the high side switches.

5. The method of claim 3, wherein performing a test adapted to verify the state of the switch of the stimulator of the EEG recording device comprises performing a test adapted to verify a state of the low side switches.

6. The method of claim 4, wherein performing the test adapted to verify the state of the high side switches comprises:
   connecting one of the high side simulator switches with one of the plurality of resistors of the hardware testing device;
   connecting the plurality of EEG electrode recording channels with the plurality of resistors of the hardware testing device;
   injecting a stimulus into the one of the high side switches, wherein the stimulus is defined by a predefined voltage level or a predefined current level;
   measuring a voltage on at least one of the plurality of EEG electrode recording channels;
   verifying that the one of the high-side switches is connected with at least one of the plurality of resistors if the measured voltage is equal to the stimulus; and
   verifying that the one of the high-side switches is not connected with any of the plurality of resistors, if the measured voltage is equal to a predefined fraction of the stimulus.

7. The method of claim 6, wherein injecting the stimulus comprises injecting a constant-voltage stimulus.

8. The method of claim 6, wherein injecting a stimulus comprises injecting a constant-current stimulus.

9. The method of claim 5, wherein performing the test adapted to verify the state of the low side switches comprises:

connecting one of the high-side switches to one of the plurality of resistors and one of the low-side switches to one of the plurality of resistors;

connecting at least one of the plurality of EEG electrode recording channels with at least one of the plurality of resistors;

injecting a stimulus into the one of the high-side switches;

measuring a voltage on at least one of the plurality of EEG electrode recording channels; and verifying that the one of the low-side switches is working if the measured voltage is at a ground potential.

10. The method of claim 9, wherein injecting the stimulus comprises injecting a constant-voltage stimulus.

11. The method of claim 9, wherein injecting a stimulus comprises injecting a constant-current stimulus.

12. The method of claim 1, wherein the at least one stimulator is located external to the EEG recording device.

13. The method of claim 1, wherein performing the channel uniqueness test for each of the plurality of EEG electrode recording channels comprises performing a lead-off functionality test.

14. The method of claim 1, wherein performing the channel uniqueness test comprises:

connecting the hardware testing device to the EEG recording device;

connecting the plurality of resistors to at least one of the plurality of EEG electrode recording channels;

determining if an electrode connected status is reported for the at least one of the plurality of EEG electrode recording channels; and determining that at least one of a recording channel uniqueness, a recording channel component, or an electrode contact viability as not working as intended if an electrode connected status is not reported for the at least one of the plurality of EEG electrode recording channels.

15. The method of claim 1, wherein performing the channel uniqueness test further comprises:

disconnecting one of the plurality of EEG electrode recording channels from one or more of the plurality of resistors; and determining if an electrode disconnected status is reported for the disconnected one of the plurality of EEG electrode recording channels.

16. The method of claim 15, wherein performing the channel uniqueness test further comprises:

determining that at least one of a recording channel uniqueness, a recording channel component, or an electrode contact viability is not working as intended if an electrode disconnected status is not reported for the disconnected one of the plurality of EEG electrode recording channels; and determining that the disconnected one of the plurality of EEG electrode recording channels is working if an electrode disconnected status is reported for the disconnected one of the plurality of EEG electrode recording channels.

17. The method of claim 1, further comprising cycling through at least one of the plurality of EEG electrode recording channels using a software executing on a computing device coupled with the hardware testing device and the EEG recording device to verify a functionality.

18. The method of claim 1, wherein performing the test for verifying the state of the switch of the at least one stimulator comprises verifying states of device switches and matrix switches.

19. The method of claim 1, wherein performing the impedance test comprises:

connecting the hardware testing device to the EEG recording device;

activating a mode within the EEG recording device to measure an impedance for each of the plurality of EEG electrode recording channels;

determining if measured impedance values match expected impedance values within a predetermined margin of error;

determining that the one or more of the plurality of EEG electrode recording channels is not working as intended if the measured impedance values do not match the expected impedance values within the predetermined margin of error; and verifying that the one or more of the plurality of EEG electrode recording channels are working as intended if the measured impedance values match the expected impedance values within the predetermined margin of error.

20. The method of claim 19, wherein the predetermined margin of error is +/−30% of the expected impedance value.

21. The method of claim 1, wherein performing the test for verifying the functionality of the electrode connections comprises:

connecting the hardware testing device to the EEG recording device;

detecting a presence or absence of a connector identification circuitry with respect to predefined groups of the plurality of EEG electrode recording channels;

determining if the connector identification circuitry is detected on the groups of the plurality of EEG electrode recording channels, wherein the detected connector identification circuitry comprises numbers and wherein each of the numbers uniquely corresponds to each of the predefined groups of the plurality of EEG electrode recording channels;

determining the connector identification circuitry as not working as intended if the connector identification circuitry is not detected on the plurality of EEG electrode recording channels; and verifying the connector identification circuitry as working as intended if the connector identification circuitry is detected on each of the plurality of EEG electrode recording channels and comprises said numbers.

22. The method of claim 21, wherein at least one of the connector identification circuitries has a polarity that is a reverse of a polarity of the other connector identification circuitries.

23. The method of claim 21, wherein each of the predefined groups comprises 4 recording channels.

* * * * *